(12) United States Patent
Rajput

(10) Patent No.: US 11,766,472 B2
(45) Date of Patent: Sep. 26, 2023

(54) METHOD OF TREATMENT FOR HAIR LOSS

(71) Applicant: Rajendrasingh Jalamsingh Rajput, Mumbai (IN)

(72) Inventor: Rajendrasingh Jalamsingh Rajput, Mumbai (IN)

(*) Notice: Subject to any disclaimer, the term of this patent is extended or adjusted under 35 U.S.C. 154(b) by 89 days.

(21) Appl. No.: 17/207,716

(22) Filed: Mar. 21, 2021

(65) Prior Publication Data

US 2022/0296684 A1 Sep. 22, 2022

(51) Int. Cl.

| | |
|---|---|
| *A61K 35/00* | (2006.01) |
| *A61K 36/00* | (2006.01) |
| *A61K 38/40* | (2006.01) |
| *A61P 17/14* | (2006.01) |
| *A61K 31/07* | (2006.01) |
| *A61K 31/593* | (2006.01) |
| *A61K 31/12* | (2006.01) |
| *A61K 31/015* | (2006.01) |

(Continued)

(52) U.S. Cl.
CPC ............ *A61K 38/40* (2013.01); *A61K 31/015* (2013.01); *A61K 31/07* (2013.01); *A61K 31/12* (2013.01); *A61K 31/122* (2013.01); *A61K 31/198* (2013.01); *A61K 31/201* (2013.01); *A61K 31/202* (2013.01); *A61K 31/375* (2013.01); *A61K 31/4045* (2013.01); *A61K 31/4172* (2013.01); *A61K 31/4188* (2013.01); *A61K 31/519* (2013.01); *A61K 31/593* (2013.01); *A61K 31/7004* (2013.01); *A61K 31/714* (2013.01); *A61K 33/00* (2013.01); *A61K 33/04* (2013.01); *A61K 33/06* (2013.01); *A61K 33/18* (2013.01); *A61K 33/26* (2013.01); *A61K 33/30* (2013.01); *A61K 33/34* (2013.01); *A61K 35/20* (2013.01); *A61P 17/14* (2018.01)

(58) Field of Classification Search
CPC ................................ A61K 35/00; A61K 36/00
See application file for complete search history.

(56) References Cited

U.S. PATENT DOCUMENTS 10,688,037 B1 * 6/2020 Morley .................. A61K 8/347

FOREIGN PATENT DOCUMENTS

WO WO-2006066323 A1 * 6/2006 ............. A61K 31/10

* cited by examiner

*Primary Examiner* — Rosanne Kosson
(74) *Attorney, Agent, or Firm* — David S. Bradin; Maynard Nexsen PC

(57) ABSTRACT

Micronutrient compositions for treating hair loss, and methods for treating hair loss by periodically administering the compositions. The micronutrients include vitamins, antioxidants, minerals, such as ferrous, calcium, and zinc salts, amino acids, fatty acids, co-enzyme Q10, biotin, omega 3, B-complex, curcumin, colostrum, lactoferrin, N acetyl cysteine, inositol, melatonin, biotin, and the like, and combinations thereof. Careful selection of doses and dosing schedules allows enhancing efficiency, preventing antagonism, reducing side effect and avoiding wastage and overdose of the micronutrients. The components support the activity of the hair growth cycle, and act as building blocks required for hair growth, lack of which can lead to slowing down and arrest of hair growth. They also help maintain inter- and intra-cellular calcium levels, reduce interference with glucose metabolism, gastric irritation and constipation in patients, and promote hair growth, without using Minoxidil or Finasteride.

19 Claims, 15 Drawing Sheets

(51) Int. Cl.
*A61K 35/20* (2006.01)
*A61K 31/375* (2006.01)
*A61K 31/122* (2006.01)
*A61K 31/519* (2006.01)
*A61K 33/26* (2006.01)
*A61K 31/202* (2006.01)
*A61K 31/4045* (2006.01)
*A61K 31/7004* (2006.01)
*A61K 31/4188* (2006.01)
*A61K 31/201* (2006.01)
*A61K 33/30* (2006.01)
*A61K 31/714* (2006.01)
*A61K 31/198* (2006.01)
*A61K 33/04* (2006.01)
*A61K 31/4172* (2006.01)
*A61K 33/18* (2006.01)
*A61K 33/00* (2006.01)
*A61K 33/34* (2006.01)
*A61K 33/06* (2006.01)

METHOD OF TREATMENT FOR HAIR LOSS

FIELD

The present disclosure generally relates to methods for treating hair loss by administering nutrient ingredients in combination comprising a main ingredient and an adjunct ingredient periodically. In particular, hair loss is treated by administering nutrient ingredients in combination comprising one or more main ingredient(s) and one or more adjunct ingredient(s) periodically, which can also reduce gastric irritation and constipation, combine synergistic nutrients to improve efficiency, avoid overdose or excess use of nutrients, in addition to promoting hair growth. Ideally, the methods can promote hair growth without requiring minoxidil or finasteride.

BACKGROUND

The background description includes information that may be useful in understanding the present invention. It is not an admission that any of the information provided herein is prior art or relevant to the presently claimed invention, or that any publication specifically or implicitly referenced is prior art.

The traditional cause of hair loss was believed to be heredity, family history and the effect of dihydrotestosterone (DHT) on sensitive hair follicle cells. The condition was therefore termed scientifically as androgenetic alopecia. Hair loss today is occurring without any hereditary or family history, and without any rise in DHT (Blume-Peytavi U, Blumeyer A, Tosti A, Finner A, Marmol V, Trakatelli M, Reygagne P, Messenger A; European Consensus Group. Si guideline for diagnostic evaluation in androgenetic alopecia in men, women and adolescents. Br J Dermatol. January; 164(1):5-15 (2011)).

There is an increasing incidence of hair loss in men and women at a relatively younger age. Increased exposure to pollution, stress, competitive life, sleep disturbances, loss of circadian rhythm, chemicals in processed foods acting as endocrine disrupting chemicals, smoking, and alcohol increase the allostatic load on the cells (Sadick N S, Callender V D, Kircik L H, Kogan S. New Insight Into the Pathophysiology of Hair Loss Trigger a Paradigm Shift in the Treatment Approach. J Drugs Dermatol. November 1; 16(11) (2017)) and disturb the internal cellular environment, causing cellular dysfunction, and weakening the cells. The weak cells become vulnerable, easily attacked by normal DHT in the circulation, leading to early hair loss.

Finasteride functions by blocking conversion of testosterone to DHT, but Finasteride is associated with side effects, resulting in a recently recognized clinical disorder known as Post Finasteride Syndrome (PFS). PFS causes depression, suicidal tendencies, and/or loss of libido, which may continue even after stopping the treatment, and may even become permanent. A recent FDA warning has been issued to this effect (Kiguradze et al., Persistent erectile dysfunction in men exposed to the 5a-reductase inhibitors, finasteride, or dutasteride, (2017)).

Minoxidil, a topically applied compound, has been approved to treat hair loss in particular androgenic alopecia, but is ineffective in sustaining the growth of new hair follicles. It has been reported that discontinuation of minoxidil treatment results in the resumption of hair loss, presumably through the loss of trophic support.

Exposure to the abovementioned external factors like pollution, stress, competitive life, sleep disturbances, loss of circadian rhythm, chemicals in processed foods acting as endocrine disrupting chemicals, smoking, and alcohol, also act as epigenetic factors that influence the genetic expression predisposing individuals to hair loss at an early age. Biologically identical twins today do not show the same extent of hair loss due to influence of epigenetic factors (Koyama T, Kobayashi K, Wakisaka N, Hirayama N, Konishi S, Hama T, Takeda K, Nakamizo Y, Kawakami M. Eleven pairs of Japanese male twins suggest the role of epigenetic differences in androgenetic alopecia. Eur J Dermatol. January-February; 23(1):113-5, (2013)). Genetic predisposition for androgenetic alopecia can now be said to be genetic by birth, or acquired by effect of epigenetic factors. Exposure to such factors alters genetic expression, promotes autoimmune response, suppresses immunity, and elicits early disorders like diabetes, hypertension, heart disease, thyroid problems, polycystic ovarian syndrome, metabolic disorders, loss of wellness, compromised cellular function and aging. Researchers refer to cellular impairment caused by these factors as the allostatic load (Mattei J, Demissie S, Falcon L M, Ordovas J M, Tucker K. Allostatic load is associated with chronic conditions in the Boston Puerto Rican Health Study. Soc Sci Med; 70(12):1988-1996, (2010)).

The increased allostatic load can be corrected by altering nutrient levels to repair cell damage, restore function, achieve homeostasis or balance of the internal cellular environment and restore cellular function to improve well-being (Lee, Kee Hyuck et al. "Relationships between Dietary Habits and Allostatic Load Index in Metabolic Syndrome Patients." Korean journal of family medicine vol. 34, 5: 334-46, (2013)). which, among other benefits, can result in hair growth.

Natural nutrition from the soil has depleted due to various, wrong agricultural practices, such as over-harvesting, lack of crop rotation, and hybrid varieties, which leads foods to lose nutritive value (Davis D R, Epp M D, Riordan H D. Changes in USDA food composition data for 43 garden crops, 1950 to 1999. Journal of the American College of Nutrition.,23:669-682, (2004)). Agriculture products are laden with chemical residues from insecticides, pesticides and fertilizers. Adding to these factors, the culture of restricted eating, dieting at an early age, fad diets, fat-free diets causing deficiency of fat-soluble vitamins and fatty acids, high-protein diets causing loss of calcium (Ioannis Delimaris, "Adverse Effects Associated with Protein Intake above the Recommended Dietary Allowance for Adults", International Scholarly Research Notices, vol. 2013, Article ID 126929, 6 pages, (2013)), and keto diets leading to biotin deficiencies, impairs the natural balance of nutrients in the body. This makes it necessary to rely on external supplementation of requisite nutrients to correct the natural balance, and restore cellular functions, that can promote well-being and manifest into visible corollary-like hair growth.

Nutritional deficiencies are reflected in the growth and quality of the hair. Hair is a barometer of health, or as it is said, hair is the mirror of health. Blood loss during menstrual cycles leads to iron deficiency in females, leading to hair loss. Restricted iron intake, intolerance to iron, and constipation can be other causes of iron loss and hair loss in females. Mal-assimilation or Mal-absorption of nutrients may also occur following prolonged acute or subacute diseases such as Irritable Bowel Syndrome.

Nutritional deficiencies also make the hair weak and susceptible to hair loss. Not all the hairs are lost at the same time. When subjected to various external factors mentioned above, weak hairs can fall out, and strong hair continues to grow initially, appearing only as increased shedding and thinning, but ultimately resulting in unnatural hair loss.

There are scientific reports of hair loss associated with nutrient deficiencies. Hence, those suffering from the hair loss turn to trying nutritional supplements one after another with little or no benefit. However, due to inter nutrient interactions and their effects, the nutrients cannot just be arbitrarily dumped on the cells. Patients indiscriminately consume antagonistic combinations and, when there is no benefit, they resort to higher doses that are of no benefit or may even reverse the beneficial actions of the nutrients and lead to adverse effects (Rogovik A L, Vohra S, Goldman R D. Safety considerations and potential interactions of vitamins: should vitamins be considered drugs? Ann Pharmacother; 44:311-24, (2010)).

Without being aware of ill effects of incorrect combinations of nutrients or their overdose, people continue to pop pills, watching advertisements and reading health articles about the need for vitamins, minerals, and supplements (Eisenberg M D, Avery R J, Cantor J H. Vitamin panacea: Is advertising fueling demand for products with uncertain scientific benefit?. *J Health Econ.*, 55:30-44 (2017)).

Food and drug administration authorities do not include nutritional supplements as drugs, so there is no consideration for inter-nutrient interactions that reduce or enhance the efficiency of the supplements. People feel that the more they consume the supplements, the better it is without being aware that this is a misunderstanding. Absorption of minerals and vitamins is dependent on their relative deficiency in the body. When some of the nutrients and vitamins are given together, they reduce the absorption of one another. High doses of vitamins, minerals and antioxidants can result in loss of efficiency (Rutkowski M, Grzegorczyk K. Adverse effects of antioxidative vitamins. International Journal of Occupational Medicine and Environmental Health, 25(2): 105-121 (2012)).

Though there are scientific reports of hair loss associated with nutrient deficiencies, or adverse effect of high doses of nutrients, there has been an unmet need for an efficient nutritional therapy to treat hair loss. The inventor of the present invention for the first time proposed the cyclical nutritional therapy for hair growth that can be applied for wellness (Rajput R, "The Concept of Cyclical Nutritional Therapy for Hair Growth Which can be Applied for Wellness," J. Nutr. Food Sci. 7:615, (2017)). In this cyclical nutrient therapy, low dose combinations of nutrients were provided each day in a 3-day cycle. Nutrients were provided as: Monday and Thursday: antioxidant, calcium, and Vitamin D3; Tuesday and Friday: iron, folic acid, Vitamin C, and Omega 3; Wednesday and Saturday: essential amino acids, B-Complex, and Biotin; and Sunday—no medicines, that is, a detox day, or an extra dose of another nutrient as per individual status if required. Such cyclical therapy has been provided, with and without finasteride and minoxidil, and has been demonstrated to show improvement in hair growth. However, excess use of antioxidants reverses the benefits and makes them pro-oxidant. Excess iron forms reactive oxygen species or free radical toxins (Elena Gammella, Stefania Recalcati, Gaetano Cairo, "Dual Role of ROS as Signal and Stress Agents: Iron Tips the Balance in favor of Toxic Effects", Oxidative Medicine and Cellular Longevity, vol. 2016, Article ID 8629024, 9 pages, (2016)) and dysregulates glucose metabolism causing insulin resistance. Excess nutrients cause gastric irritation, constipation, and overall discomfort (Beard J L. Effectiveness and strategies of iron supplementation during pregnancy. Am J Clin Nutr., May; 71(5 Suppl) (2000)). These effects cause patients to discontinue treatment, and often fail to treat certain types of hair loss, thereby leaving such patient without any effective remedy.

Accordingly, a need exists for effective nutrient regimen for treating for hair loss, which can be beneficial for different types of hair loss, ideally without using minoxidil or finasteride. Ideally, such treatments can meaningfully make supportive nutrients available to concomitantly address issues of deficiencies, improve efficiency, maintain inter and intracellular calcium levels, reduce overdose or excess use of nutrients, reduce gastric irritation, constipation and overall discomfort, and/or promote hair growth. The present invention provides such compositions and methods.

SUMMARY

In a general aspect, the present disclosure provides compositions, kits and methods for treating hair loss. The methods involve administering nutrient ingredients individually, or in combination, in such a way that they address issues of nutrient deficiencies, reduce gastric irritation, constipation and overall discomfort enhancing the efficiency while treating hair loss.

In an aspect, the present disclosure provides compositions, kits and methods for treating hair loss. The methods involve administering nutrient ingredients in combination comprising a main ingredient and an adjunct ingredient periodically, in such a way that they address issues of nutrient deficiencies, reduce gastric irritation, constipation and overall discomfort enhancing the efficiency while treating hair loss.

In a general aspect, the present disclosure provides compositions, kits and methods for treating hair loss. The methods involve administering nutrient ingredients in combination comprising a main ingredient and an adjunct ingredient periodically, in such a way that they address issues of nutrient deficiencies, reduce gastric irritation, constipation and overall discomfort enhancing the efficiency while treating hair loss.

In one aspect, the method involves administering nutrient ingredients in combination comprising one or more main ingredient(s) and one or more adjunct ingredient(s), periodically in such a way that they address issues of nutrient deficiencies, reduce gastric irritation, constipation and overall discomfort enhance the efficiency and treat hair loss.

In another aspect, the method involves periodically administering nutrient ingredients in combinations comprising one or more main ingredient(s) and one or more adjunct ingredient(s) to promote hair growth, ideally without using minoxidil or finasteride. In some embodiments, one or more ingredients are administered at altered dosages relative to dosages reported or recommended in the literature. In other embodiments, salt forms of various metal ions are used to minimize side effects observed when other salt forms, reported or recommended in the literature, were used. Examples of side effects that can be reduced include gastric irritation and constipation.

In a further aspect, the methods involve administering nutrient ingredients in combination, wherein the combination comprises one or more main ingredient(s) and one or more adjunct ingredient(s). the combinations are administered periodically to support the activity of the hair growth cycle, wherein the ingredients act as building blocks required for hair growth, the lack of which can lead to slowing down and arrest of hair growth. When administered at doses described herein, at periodic intervals as described herein, the combination of nutrient ingredients comprising one or more main ingredient(s) and one or more adjunct ingredient(s) can help prevent competitive inhibition among multiple nutrients. In one aspect of this embodiment, the nutrient ingredients include vitamins, amino acids, minerals, proteins, and lipids, and competitive inhibition is likely to occur when these are administered in certain combinations. By administering nutrient ingredients in separate combinations, comprising one or more main ingredient(s) and one or more adjunct ingredient(s), in separate administrations on different days, one can help prevent overload on the cell systems, help improve absorption, and provide improved utilization of individual nutrients.

In one aspect, the present disclosure provides a method for treating hair loss by periodically administering nutrient ingredients in combination comprising one or more main ingredient(s) and one or more adjunct ingredient(s) at prescribed doses, which can reduce gastric irritation and constipation relative to when the certain other ingredients are administered at reported or in their normally recommended dosages. Ideally, the nutrient ingredients help promote hair growth without needing to also use minoxidil or finasteride, though in some aspects, a user may also use one or both of these agents.

In another aspect, the present disclosure provides a method for treating hair loss with the help of a nutrient regimen for periodically providing a combination of nutrients, which combination comprises effective amounts of one or more main ingredient(s) and one or more adjunct ingredient(s). The nutrient ingredients, which can be selected from the group consisting of vitamins, minerals, antioxidants, amino acids, and fatty acids, are administered as a main ingredient(s) or an adjunct in a periodic manner. The components are used as an individual nutrient, or are mixed and provided as combinations.

In one aspect, the present disclosure provides a method for treating hair loss by administering nutrient ingredients comprising one or more main ingredient(s) and one or more adjunct ingredient(s) selected from but not limiting to vitamins, minerals, antioxidants, amino acids, fatty acids, and combinations thereof in a periodic manner to a patient in need of treatment thereof.

In one specific aspect, the present disclosure provides a treatment regimen for treating hair loss comprising administering the following nutrient ingredients individually, or in one or more combinations:

Composition A: comprising one or more main ingredient(s) selected from but not limiting to curcumin, colostrum, vitamin A, beta-carotene, and N acetyl cysteine; and one or more adjunct ingredient(s) selected from but not limiting to magnesium, biotin, Coenzyme Q10, calcium aspartate, calcium orate, vitamin A, vitamin D3, inositol, and melatonin Composition B: comprising one or more main ingredient(s) selected from but not limiting to ferrous bisglycinate, lactoferrin, and zinc gluconate; and one or more adjunct ingredient(s) selected from but not limiting to folic acid, vitamin C, coenzyme Q10, an omega 3 fatty acid, gama linolenic acid, and magnesium hydroxide; and Composition C: comprising one or more main ingredient(s) selected from but not limiting to histidine, glycine, lysine, arginine, ornithine, tyrosine, alanine, aspartic acid, cysteine, glutamic acid, histidine, isoleucine, leucine, methionine, phenylalanine, proline, serine, threonine, tryptophan, and valine; and one or more adjunct ingredient(s) selected from but not limiting to pyridoxine, cyanocobalamin, nicotinamide, para aminobenzoic acid, and one or more assimilable combinations of alpha tocopherol and tocotrienol.

The ingredients can be administered sequentially and separately on one or more predetermined treatment days of a week, with one or more intermittent non-treatment days each week, for the same ingredient or combination of ingredients. In one aspect, there are more non-treatment days than treatment days in any given week.

For example, Compositions A, B and C can be administered on different days of the week, with one or more days where none of these compositions is administered. The order of administration can vary. For example, Composition A can be administered on one day, followed by one or two days where no composition is administered, followed by a day where Composition B is administered, followed by one or two days where no composition is administered, followed by a day where Composition C is administered, with the total number of days being seven days.

Alternatively, Composition A can be administered, then Composition C, then Composition B, with one or two days between administrations. Alternatively, Composition B can be administered, then Composition A, then Composition C, with one or two days between administrations. Alternatively, Composition B can be administered, then Composition C, then Composition A, with one or two days between administrations. Alternatively, Composition C can be administered, then Composition A, then Composition B, with one or two days between administrations. Alternatively, Composition C can be administered, then Composition B, then Composition A, with one or two days between administrations. In each of these examples, the total number of days is seven.

In one embodiment, the treatment regimen comprises administering one or more nutrient ingredients one of the non-treatment days to an individual in need thereof.

In one embodiment, the treatment regimen comprises administering a nutrient ingredient selected from but not limiting to colostrum, lactoferrin, vitamin D3, N acetyl cysteine, and vitamin B12 on one of the non-treatment days to an individual in need thereof.

In one aspect, the method comprises administering nutrients, individually or in combination, as described herein, which can help to achieve effective reversal of miniaturization, control hair loss, thicken hair, increase hair density with growth of additional new hair, improve hair diameter and improve the rate of hair growth.

In another aspect, kits for treating hair loss are provided. The kits comprise nutrient ingredients, packaged individually and in combinations in accordance with the treatment regimens disclosed herein, for administration on pre-determined treatment days. The kits also include an insert indicating the treatment regimen for administering an individual ingredient, or specified nutrient combination, on the pre-determined treatment days, as well as an indication of the intermittent non-treatment days, as per the need of an individual.

In one aspect, the kits comprise nutrient ingredients comprising vitamins, minerals, antioxidants, amino acids, fatty acids, and combinations thereof, formulated in a suitable dosage form comprising an individual nutrient ingredient or a combination of nutrient ingredients. The ingredients are packaged separately, for administration of different compositions on different days. Included in the kit is an insert indicating the treatment regimen for administering an individual ingredient and/or specified nutrient combination on one or more pre-determined treatment days, and indicating the intermittent non-treatment days, as per the need of an individual.

In one specific aspect, the kit comprises individual packages comprising an individual nutrient ingredient, or combinations of nutrients, wherein each separate package is intended for administration on a different day.

One package comprises Composition A, which comprises one or more main ingredient(s) selected from but not limiting to curcumin, colostrum, vitamin A, beta-carotene, and N acetyl cysteine; and one or more adjunct ingredient(s) selected from but not limiting to magnesium, biotin, Coenzyme Q10, calcium aspartate, calcium orate, vitamin A, vitamin D3, inositol, and melatonin.

One package comprises Composition B, which comprises one or more main ingredient(s) selected from but not limiting to ferrous bisglycinate, lactoferrin, and zinc gluconate; and one or more adjunct ingredient(s) selected from but not limiting to folic acid, vitamin C, coenzyme Q10, an omega 3 fatty acid, gama linolenic acid, and magnesium hydroxide.

One package comprises Composition C, which comprises one or more main ingredient(s) selected from but not limiting to histidine, glycine, lysine, arginine, ornithine, tyrosine, alanine, aspartic acid, cysteine, glutamic acid, histidine, isoleucine, leucine, methionine, phenylalanine, proline, serine, threonine, tryptophan, and valine; and one or more adjunct ingredient(s) selected from but not limiting to pyridoxine, cyanocobalamin, nicotinamide, para aminobenzoic acid and gamma one or more assimilable combinations of alpha tocopherol and tocotrienol.

One optional package comprises Composition D, which comprises one or more nutrient ingredient selected from the group consisting of colostrum, lactoferrin, vitamin D3, N acetyl cysteine, and vitamin B12.

The components are formulated in suitable dosage forms, and packaged separately. The kits also include an insert indicating the treatment regimen for administering an individual ingredient and/or specified nutrient combination on pre-determined treatment days, and indicating the intermittent non-treatment days, as per the need of an individual.

These and other features, aspects, and advantages of the present subject matter will be better understood with reference to the following embodiments of the invention as set forth in the description which follows, and in part will be apparent from the description, or may be learned by the practice of the description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE DRAWINGS

The following drawings form part of the present specification and are included to further illustrate aspects of the present disclosure. The disclosure may be better understood by reference to the drawings in combination with the detailed description of the specific embodiments presented herein.

FIG. 1(a) is an image of a male subject with hair loss before treatment.

FIG. 1(b) is an image of the same male subject receiving minoxidil and finasteride treatment after four months.

FIG. 1(c) is an image of the same male subject receiving minoxidil and finasteride treatment after twelve months.

FIG. 1(d) is an image of a male subject with hair loss before nutrient treatment with one embodiment of the methods described herein.

FIG. 1(e) is an image of the same male subject receiving nutrient treatment in accordance with one embodiment of the methods described herein after four months.

FIG. 1(f) is an image of the same male individual receiving nutrient treatment regimen in accordance with one embodiment of the methods described herein after twelve months.

FIG. 1(g) is an image of a female subject with hair loss before treatment.

FIG. 1(h) is an image of a female subject with hair loss before treatment.

FIG. 1(i) is an image of the same female subject receiving minoxidil treatment after four months.

FIG. 1(j) is an image of the same female subject receiving minoxidil treatment after twelve months.

FIG. 1(k) is an image of the same female subject receiving nutrient treatment regimen in accordance with one embodiment of the methods described herein after four months.

FIG. 1(l) is an image of the same female subject receiving nutrient treatment regimen in accordance with one embodiment of the methods described herein after twelve months.

FIGS. 2 (a)-g are photographs comparing treatment with a once-a-day iron supplement in a female subject with treatment of hair loss in accordance with one embodiment of the methods described herein.

FIGS. 3 (a)-(h) are photos showing a comparison of treatment with a cyclic therapy and treatment of hair loss in accordance with one embodiment of the methods described herein in male and female subjects.

FIGS. 4 (a)-(b) are photos comparing a female subject suffering from poly cystic ovarian disease (PCOD) before and after treatment of hair loss in accordance with one embodiment of the methods described herein.

FIGS. 5 (a)-(d) are images comparing two female subjects suffering from hair loss due to thyroid dysfunction before and after treatment of hair loss in accordance with one embodiment of the methods described herein.

FIGS. 6 (a)-(b) are images comparing hair loss due to diffuse alopecia areata before and after treatment of hair loss in accordance with one embodiment of the methods described herein.

FIGS. 7 (a)-(b) are images comparing hair loss due to alopecia areata before and after treatment of hair loss in accordance with one embodiment of the methods described herein.

FIGS. 8 (a)-(b) are images comparing hair loss due to pollution before and after treatment of hair loss in accordance with one embodiment of the methods described herein.

FIGS. 9 (a)-(b) are images comparing hair loss due to miniaturization before and after treatment of hair loss in accordance with one embodiment of the methods described herein.

FIGS. 10 (a)-(b) are images comparing hair loss due to smoking before and after treatment of hair loss in accordance with one embodiment of the methods described herein.

FIGS. 11 (a)-(b) are images comparing hair loss due to trichotillomania before and after treatment of hair loss in accordance with one embodiment of the methods described herein.

DETAILED DESCRIPTION

Figure 1A:
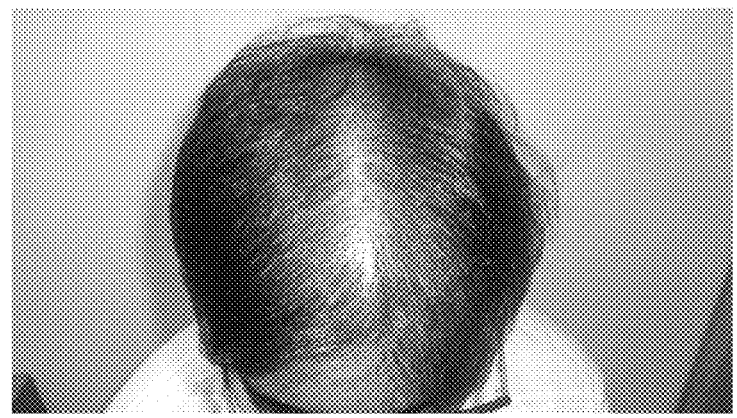
FIGS. 1(a)-(l) are images taken from a comparative study which compared treatment of a male subject with Finasteride and Minoxidil, and a female subject with Minoxidil, with treatment of hair loss in accordance with one embodiment of the methods described herein.

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, and so forth, used to describe and claim certain embodiments of the invention are to be understood as being modified in some instances by the term "about." The term "about" is some of the embodiments may mean +10% of the respective figure or value or amount. Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability.

All methods described herein can be performed in suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The headings and abstract of the invention provided herein are for convenience only and do not interpret the scope or meaning of the embodiments.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Various terms are used herein. To the extent a term used in a claim is not defined below, it should be given the broadest definition persons in the pertinent art have given that term as reflected in printed publications and issued patents at the time of filing.

The terms "administer," "administering" and "administration" as used herein refer to either directly administering a compound (also referred to as an agent of interest) or pharmaceutically acceptable salt of the compound (agent of interest) or a composition to a subject.

The terms "patient" and "subject" are interchangeable and may be taken to mean any living organism which may be treated with compounds or compositions provided for herein. As such, the terms "patient" and "subject" may comprise, but is not limited to, any non-human mammal, primate or human. In some embodiments, the patient or subject is a human.

The terms "pharmacologically effective amount" or "therapeutically effective amount" refer to a non-toxic, but sufficient amount of the ingredient to provide the desired level in the bloodstream or at the site of action (e.g. intracellularly) in the subject to be treated, and/or to provide a desired physiological, biophysical, biochemical, pharmacological or therapeutic response, such as diminution of hair loss and/or amelioration of the manifestations of hair growth. The exact amount required will vary from subject to subject, and will depend on numerous factors, such as the ingredient or combination of ingredients used, the administration period or frequency; as well as patient considerations, such as age, sex, cause, general condition of the subject, and the severity of the condition that is hair loss being treated, and the like. An appropriate "effective" amount in any individual case may be determined by one of ordinary skill in the art using routine experimentation, based upon the information provided herein.

"Pharmaceutically acceptable excipient or carrier" refers to an excipient that may optionally be included in the compositions of the invention and that causes no significant adverse toxicological effects to the patient.

"Main ingredient" refers to a nutrient ingredient intended to cure the deficiency of that ingredient or supplement said nutrient ingredient to provide a desired physiological, biophysical, biochemical, pharmacological or therapeutic response, such as diminution of hair loss and/or amelioration of the manifestations of hair growth.

"Adjunct ingredient" refers to a nutrient ingredient intended to supplement the main nutrient ingredient in eliciting a desired physiological, biophysical, biochemical, pharmacological or therapeutic response, such as diminution of hair loss and/or amelioration of the manifestations of hair growth.

The present disclosure provides methods for treating hair loss by administering nutrient ingredients, individually or in combination, in relatively low doses, in such a way that they reduce the dose but enhance the efficiency and prevent antagonism, avoid wastage and overdose of the nutrients, support the activity of the hair growth cycle and/or act as building blocks required for hair growth, lack of which can lead to slowing down and arrest of hair growth.

In one embodiment, the methods comprise administering nutrient ingredients comprising a main ingredient and an adjunct ingredient periodically, which can help prevent competitive inhibition among multiple nutrients including vitamins, minerals, amino acids, fatty acids that can occur when given in combination; prevent overload on the cell systems; help in absorption and improve utilization of individual nutrients.

In one embodiment, the methods involve periodically administering nutrient ingredients comprising a main ingredient and an adjunct ingredient, which can address issues of nutrient deficiencies, maintain inter and intra-cellular calcium levels, gastric irritation, constipation, and overall discomfort, avoid overdose or excess use of nutrients and/or promote hair growth, without needing to use minoxidil or finasteride.

In one embodiment, nutrient ingredients are provided in an effective amount, and selected from the group consisting of vitamins, minerals, antioxidants, amino acids, fatty acids, periodically, wherein the nutrients are used as an individual nutrient, or are mixed and provided as combinations of nutrients.

In some embodiments, the methods a) effectively neutralize free radicals that accumulate as toxins formed out of various metabolic processes in the body, b) create an environment conducive to promoting new growth of hair follicle cells, c) provide amino acids essential for forming the keratin protein for the structure of new growing hair, d) provide vitamins required as catalysts in hair building and cell growth processes, and/or e) provide minerals that act as catalysts and cementing substances in the formation of new hair shafts.

In some embodiments, the nutrient ingredients comprise an effective amount of minerals, vitamins, antioxidants, amino acids, and fatty acids. The ingredients can be used individually as separate components that are administered simultaneously, successively or intermittently, or in the form of a composition comprising a combination of ingredients that can be mixed prior to use or formulated in a suitable dosage form for administration to an individual in need thereof.

In an embodiment, the minerals are selected from the group consisting of zinc, calcium, magnesium, iron, manganese, phosphorus, copper, sulfur, sodium, potassium, selenium, silicon, iodine, cobalt, molybdenum, vanadium, chromium or the like, or combination thereof.

Representative amino acids include, but are not limited to, alanine, arginine, aspartic acid, cysteine, glutamic acid, glycine, histidine, isoleucine, leucine, lysine, methionine, phenylalanine, serine, threonine, proline, tryptophan, tyrosine, valine and/or their salts, and the like, or combinations thereof.

Omega-3 fatty acids are a representative example of a fatty acid. Representative omega-3 fatty acids include, but are not limited to, eicosapentaenoic acid (EPA) and docosahexaenoic acid (DHA). Other representative fatty acids include alpha lipoic acid, alpha-linoleic acid and omega-6 fatty acids, such as gamma linoleic acid. Combinations of fatty acids can also be used.

Representative vitamins include, but are not limited to, vitamin A, vitamin B Complex, vitamin C, vitamin D, vitamin E, vitamin K, and the like, and combinations thereof.

Representative vitamin B include, but are not limited to, thiamin, riboflavin, niacin, pantothenic acid, pyridoxine, biotin, folic acid, and cyanocobalamin.

Representative antioxidants include, but are not limited to, colostrum, vitamin A, beta-carotene, N acetyl cysteine, alpha tocopherol, tocotrienol, coenzyme Q10, curcumin, lactoferrin, melatonin, catechin, proanthocyanidin, glutathione, flavonoids, polyphenols, and the like, and combinations thereof.

In one embodiment, the method comprises periodically administering to a person in need thereof nutrient ingredients selected from the group consisting of vitamins, minerals, antioxidants, amino acids, fatty acids, or any combination thereof, according to a treatment regimen. The ingredients can be administered individually or in one or more combinations.

In one embodiment, a nutrient regimen for treating hair loss comprises providing one or more main ingredient(s) and one or more adjunct ingredient(s) in an effective amount periodically. The nutrient ingredients, selected from the group consisting of vitamins, minerals, antioxidants, amino acids, and fatty acids, are administered as a main ingredient(s) or an adjunct ingredient in a periodic manner. The components are used as an individual nutrient, or are mixed and provided as combinations.

In one specific embodiment, the present disclosure provides the treatment regimen for treating hair loss comprising administering the following nutrient ingredients individually, or in one or more combinations:

Composition A: comprising one or more main ingredient(s) selected from but not limiting to curcumin, colostrum, vitamin A, beta-carotene, and N acetyl cysteine; and one or more adjunct ingredient(s) selected from but not limiting to biotin, Coenzyme Q10, calcium aspartate, calcium orate, vitamin D3, inositol, and melatonin;

Composition B: comprising one or more main ingredient(s) selected from but not limiting to ferrous bisglycinate, lactoferrin, and zinc gluconate; and one or more adjunct ingredient(s) selected from but not limiting to folic acid, vitamin C, coenzyme Q10, an omega 3 fatty acid, gama linolenic acid, and magnesium hydroxide; and Composition C: comprising histidine, glycine, lysine, arginine, ornithine, and tyrosine; and one or more adjunct ingredient(s) selected from but not limiting to pyridoxine, cyanocobalamin, nicotinamide, para aminobenzoic acid and hydroxide; one or more assimilable combinations of alpha tocopherol and tocotrienol.

These combinations can be administered sequentially, and separately, on one or more pre-determined treatment days of a week with one or more intermittent non-treatment days in the week for the same ingredient or combination. Ideally, there are more non-treatment days than treatment days in any given week.

The same combination of ingredients can be administered more than once in a week, with the proviso that none of the combinations are administered simultaneously on the same day.

In certain embodiments, the compositions comprise:

Compositions A comprising combination of main ingredient(s) with adjunct ingredient(s) can be selected from but not limiting to:
curcumin with biotin;
colostrum with coenzyme Q10; vitamin A, beta-carotene with calcium aspartate, calcium orate and vitamin-D3 (more generally, an antioxidant, a calcium salt, and vitamin D3); or
N-acetyl cysteine with inositol and melatonin.

Compositions B comprising main ingredient(s) with adjunct ingredient(s) selected from but not limiting to:
ferrous bisglycinate with vitamin C, folic acid (more generally, an iron salt, folic acid, Vitamin C, and an Omega 3 fatty acid);
lactoferrin with omega-3-fatty acid;
zinc gluconate with gama linolenic acid; or
zinc gluconate with magnesium hydroxide.

Compositions C comprising main ingredient(s) with adjunct ingredient(s) selected from but not limiting to: L-histidine hydrochloride, glycine, and lysine mono HCl with pyridoxin HCl; L-arginine, L-ornithine with cyanocobalamin; tyrosine with nicotinamide; or L-arginine, L-ornithine with para amino benzoic acid and assimilable combinations of alpha tocopherol and tocotrienol, and, more generally, one or more essential amino acids, B-Complex, and Biotin.

In One Embodiment, the Compositions Comprise:
Composition A: a magnesium salt, colostrum, curcumin, a calcium salt, vitamin A, vitamin D3, and beta-carotene;
Composition B: lactoferrin, vitamin C, Co enzyme Q10, omega 3 fatty acid, folic acid and one or more assimilable ferrous salts; and Composition C: melatonin, inositol, biotin, gamma linoleic acid, amino acids, vitamins B and one or more assimilable combinations of alpha tocopherol and tocotrienol.

The administration of the individual compositions is temporally spaced apart by a period of one, or two or three or more days from each other. In this embodiment, all three combinations are administered within the same week, and each combination is administered one or two times in a week.

In one embodiment, the composition A can be administered on Treatment Day 1, and subsequently on Treatment Day 3 or 4 of the same week, with the proviso that no other combination of ingredients is administered on the same day.

In another embodiment, the composition B is administered on Treatment Day 2, and, subsequently, on Treatment Day 4 or 5 of the same week, with the proviso that no other combination of ingredients is administered on the same day.

In yet another embodiment, the composition C is administered on Treatment Day 3, and, subsequently, on Treatment Day 5 or 6 of the same week, with the proviso that no other combination of ingredients is administered on the same day.

In yet another embodiment, the treatment regimen comprises administering on one or more pre-determined treatment days or non-treatment days one or more additional nutrient ingredients, individually or as a part of the specific combination. The one or more additional nutrient ingredients are selected from the group consisting of minerals, vitamins, antioxidants, amino acids, fatty acids, macronutrients, adjuvants, and any additional ingredient as per the need of an individual for treating hair loss, and combinations thereof.

In one embodiment, the treatment regimen comprises administering on one or more pre-determined treatment days or non-treatment days one or more further nutrient ingredients, individually or as a part of the specific combination. The further nutrient ingredients are selected from the group consisting of one or more ferrous salts, one or more magnesium salts, vitamin D3, Co enzyme Q10, and combinations thereof.

In various embodiments, the treatment regimens, comprising specific combinations of the nutrient ingredients as described herein, are included in an amount to be effective, and which can prevent or at least minimize competitive inhibition among multiple nutrients, such as vitamins, minerals and other nutrients. Competitive inhibition is likely to occur if all nutrients are administered on the same day. By controlling the dosage, and distributing different nutrients over different days of the week, one can also minimize or prevent overload on the cell systems, ensuring better absorption and utilization of individual nutrients.

In various embodiments, the amount of each individual nutrient ingredient to be administered is calculated based on the following weight basis:

a zinc salt in the range of from about 20 mg to about 50 mg, in one embodiment, zinc gluconate at a dosage of 20-40 mg, or zinc sulfate at a dosage of around 15 mg, colostrum in the range of from about 150 mg to about 250 mg, for example, around 200 mg, a magnesium salt in the range of from about 50 mg to about 250 mg, such as 100 mg or 200 mg, an example of which is magnesium oxide, or, alternatively, in a dosage of around 5 mg, a calcium salt in the range of from about 400 mg to about 800 mg, such as around 500 mg, a ferrous salt in the range of from about 75 mg to about 150 mg, such as 83 mg, an example of which is ferrous fumarate, and in another embodiment, in a range of around 14 mg.

a selenium salt in the range of from about 100 mg to about 200 mg, an example of which is selenium dioxide, which, in another embodiment, is present in an amount of around 30 mcg, curcumin in the range of from about 180 mg to about 300 mg, for example, around 250 mg, beta-carotene in the range of from about 20 mg to 75 mg, for example, around 30 mg, lactoferrin in the range of from about 75 mg to 150 mg, for example, around 110 mg, melatonin in the range of from about 20 mg to 70 mg, for example, around 50 mg, Coenzyme Q10 in the range of from about 25 mg to 50 mg, for example, around 30 mg, One or more omega 3 fatty acids in the range of from about 200 mg to about 800 mg, for example, around 300 mg, alpha lipoic acid in the range of from about 1 mg to about 2 mg, gamma linoleic acid in the range of from about 100 mg to about 300 mg, for example, around 200 mg, N acetyl cysteine in the range of from about 180 mg to about 400 mg, for example, around 200 mg, or, in an alternative embodiment, a lower dose of around 3.9 mg, tyrosine in the range of from about 5 mg to about 15 mg, for example, around 12 mg, lysine in the range of from about 10 mg to about 50 mg, for example, between around 20 and 25 mg, L-ornithine in the range of from about 50 mg to about 100 mg, for example, around 75 mg, L-arginine in the range of from about 50 mg to about 250 mg, for example, around 125 mg, and in another embodiment, around 25 mg, L-histidine in the range of from about 5 mg to about 25 mg, for example, between around 7.5 to 15 mg, taurine in the range of from about 180 mg to about 350 mg, glycine in the range of from about 5 mg to about 10 mg, or between around 10 and 15 mg, para amino benzoic acid in the range of from about 100 mg to about 350 mg, for example, around 275-285 mg, folic acid in the range of from about 50 mcg mg to 150 mcg, for example, around 100 mcg, or, alternatively, around (200 mcg), inositol in the range of from about 25 mg to 75 mg, for example, around 50 mg, biotin in the range of from about 20 mg to about 75 mg, for example, around 50 mg, or in another embodiment, around 0.15 mg, nicotinamide in the range of from about 10 mg to 20 mg, for example, between around 14 and 18 mg, pyridoxine HCl (Vitamin B6) in the range of from about 0.5 mg to 4 mg, preferably between around 1.5 and 2 mg, calcium D—pantothenate in the range of from about 20 mg to about 60 mg, or, in another embodiment, between about 5 and about 10 mcg, vitamin B12 in the range of from about 0.5 mcg to about 5 mcg, for example, around 1 mcg, vitamin C in the range of from about 100 mg to about 500 mg, for example, between around 200 and 400 mg, or, in another embodiment, around 60 mg, vitamin D3 in the range of from about 350 IU to about 75000 IU, for example, between around 400 and 50,000 IU, and in another embodiment, around 200 IU, vitamin A in the range of from about 1200 IU mg to about 2500 IU, for example, around 2000 IU, an alpha tocopherol, such as Vitamin E acetate, in a range of from about 60 mg to about 210 mg, or, in another embodiment, around 10 mg, tocotrienol in the range of from about 60 mg to about 210 mg, sulfur, as methylsufonylmethane (MSM) in the range of from about 125 mg to about 200 mg, copper oxide in the range of from about 0.5 mg to about 2 mg, or copper sulfate in an amount of around 2 mg, manganese sulfate monohydrate in the range of from about 1 mg to about 2 mg, or magnesium oxide in a range of around 5 mg, iodine as potassium iodide in the range of from about 80 mg to about 160 mg, or, alternatively, around 0.15 mg, molybdenum picolinate in the range of from about 0.5 mg to 1.5 mg, or sodium molybdate in an amount of around 25 mcg, vanadium citrate in the range of from about 10 mg to about 25 mg, chromium polynicotinate in the range of from about 125 mg to about 250 mg, or chromium Picollinate in an amount of around 25 mcg, catechin in the range of from about 80 mg to about 160 mg, and proanthocyanidin in the range of from about 40 mg to about 80 mg.

In one embodiment, where calcium is used, it is used as a combination of two or more calcium salts, such as calcium aspartate and calcium orate, and the like.

In one embodiment, the ferrous salt is ferrous bisglycinate. In one embodiment, the zinc salt is zinc gluconate.

In one embodiment, the antioxidants, omega-3 fatty acid, and amino acid are only administered two or three days per week.

Kits

In another embodiment, the present disclosure relates to a kit for treating hair loss. The kit comprises nutrient ingredients packaged individually or in combinations, in accordance with the treatment regimens described herein. The kits include individual packages of nutrients to be administered on pre-determined treatment day(s).

The kits also include inserts indicating the treatment regimen for administering an individual ingredient and/or specified nutrient combination on pre-determined treatment days, and indicating the intermittent non-treatment days, as per the need of an individual.

In one embodiment, the kit comprises nutrient ingredients comprising vitamins, minerals, antioxidants, amino acids, fatty acids, or any combination thereof, formulated in a suitable dosage form, comprising an individual nutrient ingredient or a combination of nutrient ingredients and packaged separately. An insert is included in the kit, which indicates the treatment regimen for administering an individual ingredient and/or specified nutrient combination on the pre-determined treatment days and indication of the intermittent non-treatment days, as per the need of an individual.

In another embodiment, the kit comprises an individual nutrient ingredient, or combinations of nutrients, comprising:

Composition A: comprising one or more main ingredient(s) selected from but not limiting to curcumin, colostrum, vitamin A, beta-carotene, and N acetyl cysteine; with one or more adjunct ingredient(s) selected from but not limiting to biotin, Coenzyme Q10, calcium aspartate, calcium orate, vitamin D3, inositol, and melatonin;

Composition B: comprising one or more main ingredient(s) selected from but not limiting to ferrous bisglycinate, lactoferrin, and zinc gluconate; with one or more adjunct ingredient(s) selected from but not limiting to folic acid, vitamin C, coenzyme Q10, an omega 3 fatty acid, gama linolenic acid, and magnesium hydroxide; and Composition C: comprising histidine, glycine, lysine, arginine, ornithine, and tyrosine; with one or more adjunct ingredient(s) selected from but not limiting to pyridoxine, cyanocobalamin, nicotinamide, para aminobenzoic acid and one or more assimilable combinations of alpha tocopherol and tocotrienol.

In certain embodiment, the kit comprises an individual nutrient ingredient, or combinations of main ingredient(s) with adjunct ingredient(s) nutrients, comprising:

Composition A Selected From:
curcumin with biotin;
colostrum with coenzyme Q10; vitamin A, beta-carotene with calcium aspartate, calcium orate and vitamin-D3; or
N-acetyl cysteine with inositol and melatonin.

Composition B Selected From:
ferrous bisglycinate with vitamin C, folic acid;
lactoferrin with omega-3-fatty acid; zinc gluconate with gama linolenic acid; or
zinc gluconate with magnesium hydroxide.

Composition C Selected From:
L-histidine hydrochloride, glycine, and lysine mono HCl with pyridoxin HCl;
L-arginine, L-ornithine with cyanocobalamin; tyrosine with nicotinamide; or
L-arginine, L-ornithine with para amino benzoic acid and one or more assimilable combinations of alpha tocopherol and tocotrienol.

In One Embodiment, the Kit Comprises:
Composition A: magnesium, colostrum, curcumin, calcium, vitamin A, vitamin D3, and beta-carotene;
Composition B: lactoferrin, vitamin C, Co enzyme Q10, omega 3 fatty acid, folic acid and one or more assimilable ferrous salts;
Composition C: melatonin, inositol, biotin, gamma linoleic acid, amino acids, and vitamins B; with one or more assimilable combinations of alpha tocopherol and tocotrienol; and optionally,
Composition D: Vitamin D3.

The different compositions listed above are formulated in suitable dosage forms and packaged separately. The kit also includes an insert indicating the treatment regimen for administering an individual ingredient and/or specified nutrient combination on the pre-determined treatment days, and indicates the intermittent non-treatment days, as per the need of an individual.

In one embodiment, the kit further comprises one or more zinc salts, which can be packaged separately from the other compositions, with instructions that the zinc salts are to be administered on pre-determined treatment days and non-treatment days, with a gap of one day per week. In one embodiment, the kit comprises the individual ingredient to be administered separately, and combinations of nutrients to be administered simultaneously, formulated in suitable dosage forms and packaged separately.

Methods of Treating Hair Loss

The method of treating hair loss explore two sides of having more hair. Either fight the fall or increase the growth. Only a small percentage of hair suffer fall in every cycle. Balding is not caused by hair fall but the lack of replacement of the fallen hair with new hair as the hair cycle is disrupted or dysregulated or arrested. The treatment regimen in accordance with the present disclosure targets to restore cell function and reduce the frequency of excessive hair loss and promote the replacement of fallen hair with new hair. The extension of the inactive resting phase or the telogen phase into the empty follicle phase or kinogen phase is responsible for the hairless spots and hair thinning appearance (Guarrera M, Rebora A. The Higher Number and Longer Duration of Kenogen Hairs Are the Main Cause of the Hair Rarefaction in Androgenetic Alopecia. Skin Appendage Disord., 5(3): 152-154, (2019)).

These inactive follicles are not dead. The follicles are dormant because the internal cellular environment is not favorable for rapid cell division and growth. The inactive follicles can be recruited back into the growth phase if the internal cellular environment is restored to become conducive to hair growth and there is provision for the required nutrition and building blocks for the hair cells to divide and grow.

The methods described herein are effective in treating different types of hair falls, including all levels of hair loss from grade 1 to grade 7, in all age groups from 19 to 73 years, irrespective of an individual's sex. Using the treatments described herein, hair loss can be controlled, existing hair growth can be improved, and hair in dormant or resting phase can be manifested to regrowth. Hair growth can be restored in areas that have some residual hair. However, in most cases, a completely bald shiny patch with no living roots, where the follicles are dead, cannot regrow hair, whether using the methods described herein, or using prevailing conventional therapies.

The methods described herein can effectively reverse miniaturization, control hair loss, thicken hair, improve the rate of hair growth, increase hair density with growth of additional new hair, and improve hair diameter.

The methods described herein can provide a therapeutic benefit of new hair growth, within a period of 1 month or two months, as compared to known drugs such as finasteride and/or minoxidil, which typically takes 6-12 months to show the same results.

The treatment regimens described herein can be beneficial for young persons who are not candidates for hair transplant, these patients can grow back 30-40% of their lost hair without a hair transplant surgery, thus avoid the need for surgery. For those with advanced baldness who do require surgery the treatment regimen can strengthen the hair to result in better growth and prevent post-surgical sudden hair shading which is a common post-hair transplant loss complication termed as shock.

The treatment regimens described herein can be used to treat diffuse thinning, increased hair fall during washing or combing, weak hair, slow growing hair, breaking of hair due to chemical damage or hair abused with hair dryers, straightening, perming, dyeing, thyroid-related hair loss, post-pregnancy hair loss, anxiety and stress-related hair loss, iron deficiency hair loss, protein deficiency hair loss, nutritional hair loss, post-surgical hair loss, hair loss due to prolonged illness, hair loss due to diabetes, hormonal hair loss, hair loss due to smoking and tobacco, hair loss due to stress, hair loss due to pollution, hair loss due to electromagnetic or cell phone radiation, hair loss due to side effects of prolonged medications, hair loss due to dieting or likes and dislikes for certain foods, and the like.

The treatment regimens described herein can be used to treat hair loss for persons recovering from major surgery, bypass, heart patients, diabetic patients, health conscious persons who want to take iron, calcium, vitamin after the age of 40, gastric banding patients, persons on weight loss programs and other situations where nutritional support is required.

The treatment regimens described herein can be used for better health and well-being, and the nutrient combinations can be tailored to provide adjuvant therapy along with conventional treatment of diabetes, anemia, heart disease, PCOD, thyroid disorders, respiratory disorders, boosting immunity and support for autoimmune disorders. In this manner, the compositions and methods described herein provide a novel way of delivering nutrients with relatively lower doses and enhanced efficiency, avoiding inter-nutrient interactions, promoting synergistic nutrient combinations, and avoiding use of antagonistic nutrients from being paired together.

Although the subject matter has been described in considerable detail with reference to certain preferred embodiments thereof, other embodiments are possible. The present invention is not intended to be limited by the following non-limiting examples.

EXAMPLES

The disclosure will now be illustrated with working examples, which are intended to illustrate the working of the disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and combinations, the exemplary methods, devices and materials are described herein. It is to be understood that this disclosure is not limited to particular methods, and experimental conditions described, as such methods and conditions may vary.

There are individual studies and reports of experimental or clinical benefit from the use of nutritional supplements that my benefit one of the many aspects of hair loss management with varying degree of success, however, none have attempted to create a synergistic low dose sequential program or a clinical regimen that includes a comprehensive, safe and effective use of these supplements in order to deliver consistent results as is demonstrated in the examples that follow.

Example 1

Controlled Clinical Trial Comparing Minoxidil and Finasteride in Men and Minoxidil Alone in Women and a Nutrient Treatment Regimen in Accordance with one Embodiment Described Herein This controlled clinical trial compares the current treatment for hair loss within two controlled groups for both men and women against the use of one embodiment of the nutritional therapy regimen described herein. One hundred patients in each of the 4 groups, a total of 400 patients, were followed for 1 year. The progress was evaluated every 2 months with computerized measurements of hair density, hair caliber, global photography and uniquely designed self-assessment scores.

Group 1 CM: Control group for men (CM) consisted of 100 volunteer male patients who were between 25 to 50 years of age and had hair loss between Norwood Hamilton grade III to grade V. The male control group received 1 mg finasteride every day and application of 2% minoxidil lotion 2 times a day, 1 mL in the morning after bath and 1 mL in the evening before sleep every day.

Group 2 CW: Control group for women (CW) consisted of 100 volunteer female patients who were between 25 to 50 years of age and had hair loss Ludwig grade II and III. The female control group did not receive finasteride but were prescribed the application of 2% minoxidil lotion 1 mL, 2 times a day, morning after bath and evening before sleep.

Group 3 TM: Treatment group for 100 men (TM) and
Group 4 TW: treatment group for 100 women (TW)

Treatment groups for both men and women followed the same protocol. Patients in both the groups did not receive finasteride or minoxidil. Treatment groups received the following nutrient treatment regimen combinations:

a) a combination comprising magnesium hydroxide (100 mg), colostrum (Natural Health Organics, Australia) (200 mg), curcumin synthetic (250 mg), one or more calcium salts (500 mg), vitamin A (2000 IU), vitamin D3 (400 IU), and beta-carotene (BASF Australia Ltd., Australia) (30 mg) ($1^{st}$ and $4^{th}$ day);

b) a combination comprising lactoferrin (110 mg), vitamin C (400 mg), Co enzyme Q10 (30 mg), omega 3 fatty acid (VivoMega™, GC Rieber Oils AS, Norway) (300 mg), folic acid (100 mcg and ferrous bisglycinate (83 mg) ($2^{nd}$ and $5^{th}$ day);

c) a combination comprising melatonin (50 mg), inositol (50 mg), biotin (50 mg), gamma linoleic acid (200 mg), L-histidine hydrochloride (7.7 mg), glycine (10 mg), lysine mono HCl (25 mg), L-arginine (125 mg), L-ornithine(75 mg), tyrosine (11.9.mg), pyridoxine HCl (1.5.mg), cyanocobalamin (1 mcg), nicotinamide (14 mg), and para amino benzoic acid (280.mg) ($3^{rd}$ and $6^{th}$ day).

The age distribution and grade of hair loss of the patients is summarized in Tables 1 & 2.

TABLE 1

Age distribution of patients in the study

| Age (years) | Male (%) | Female (%) |
|---|---|---|
| 25-30 | 32 | 36 |
| 30-40 | 47 | 40 |
| 40-50 | 21 | 24 |

TABLE 2

Grade of hair loss in male & female patients in the study

| | Control group (%) | Treatment group (%) |
|---|---|---|
| Grade III | 30 | 32 |
| Grade IV | 50 | 48 |
| Grade V | 20 | 20 |
| Ludwig II | 48 | 46 |
| Ludwig III | 52 | 54 |

Evaluation of the results was done by global photography, computerized hair analysis carried out every 2 months and patient self scores at the completion of the study (Table 3).

TABLE 3

Patient's self-assessment scoring chart

| Criteria | Score |
|---|---|
| Area has become worse than before | −1 |
| Area looks the same | 0 |
| Hair loss is under control | 1 |
| Area looks better than before | 1 |
| Area is showing new hair growth | 1 |
| Area of hair loss has become smaller than before | 1 |
| Friends and others are noticing the difference | 1 |

Results:

Improvement seen in control groups and treatment groups is summarized in Table 4.

TABLE 4

Results in Control and treatment groups at 4 months and 12 months

| Criteria | Male Control Group | | Male Treatment Group | | Female Control Group | | Female Treatment Group | |
|---|---|---|---|---|---|---|---|---|
| | 4 mths | 12 mths | 4 mths | 12 mths | 4 mths | 12 mths | 4 mths | 12 mths |
| Control of Hair fall | No relief | 27% | 68% in 4 weeks | 85% | No relief | 22% | 59% in 4 weeks | 76% |
| Density | 9% | 11% | 34% | 76% | 10% | 16% | 38% | 70% |
| Caliber | 7% | 14% | 29% | 63% | 8% | 12% | 34% | 58% |
| No Benefit | 45% | 42% | — | — | 31% | 26%% | — | — |
| High Self score | — | — | — | 70% | — | — | — | 62% |
| Low Self score | — | 23% | — | — | — | 14% | — | — |
| Worsened | — | 13% | — | — | — | 15% | — | — |

Improvement in hair density and caliber was found to begin early within 2 months in men and women in the treatment groups having nutritional supplements. Use of different nutrients on different days prevents hyper-vitamins is allowing the patients to continue the treatment for a long time and obtain significantly better results.

Figure 1B:
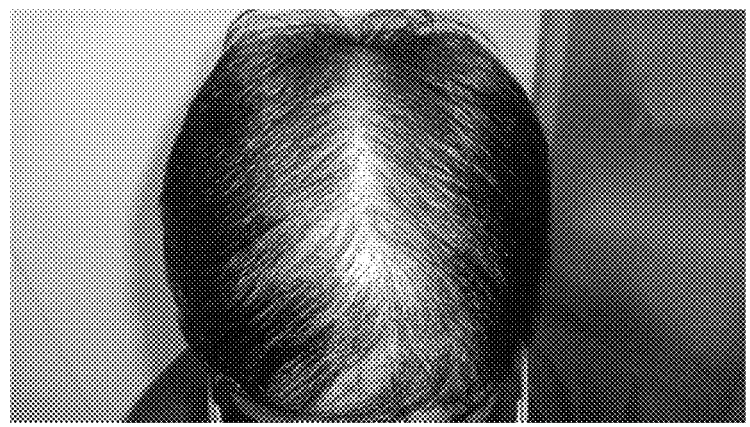
Figure 1C:
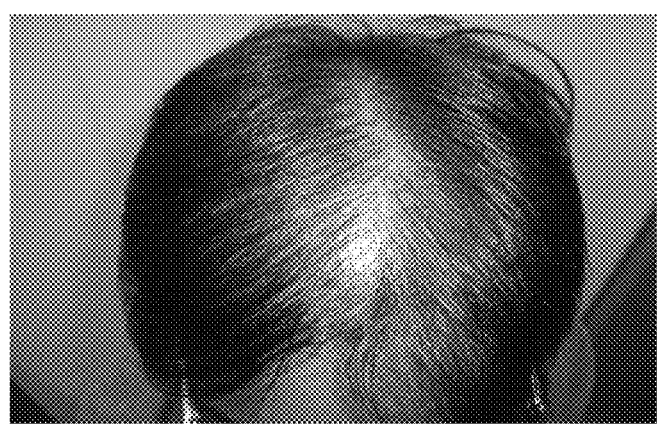

In the control groups, hair growth started after 4-6 months, which is the standard time frame required for the effect of finasteride and minoxidil, wherein only caliber improved marginally without any noticeable effect on hair density. The same is evident from FIGS. 1(a) and (g), which are images of a male and female subjects respectively with hair loss before treatment and FIGS. 1(b) and (h), which are images of the same male subject receiving minoxidil and finasteride treatment and the same female subject receiving minoxidil treatment respectively after four months. The benefit with finasteride and minoxidil alone was slow and the maximum growth achieved in the control groups was below 50% of the improvement achieved in the treatment group. The results are similar to long-term studies on the use of finasteride, which have reported 48-59% improvement (FIG. 1(c) and FIG. 1(j)) with 41-52% non-responders at the end of 1 year, and 17% of patients having deteriorated with hair loss more than the initial status after one year. The minoxidil group complained of hair loss for 8-10 weeks, which can be due to initial increased shedding known to happen with minoxidil during the phasing period. The shedding creates a lack of confidence among patients, who then insist that the hair loss is severe and unremitted for a longer duration. Minoxidil only extends the growth phase of hair, that does not translate to hair growth. Hence, results seen were less and slower, that also created some non-responders in this group. The side effects observed with the control group included complaints of scalp irritation, dryness, itching, and frizzy hair after Minoxidil application, which are known side effects of Minoxidil. Loss of libido was reported by a few patients, which is a known side effect of Finasteride.

Figure 1D:
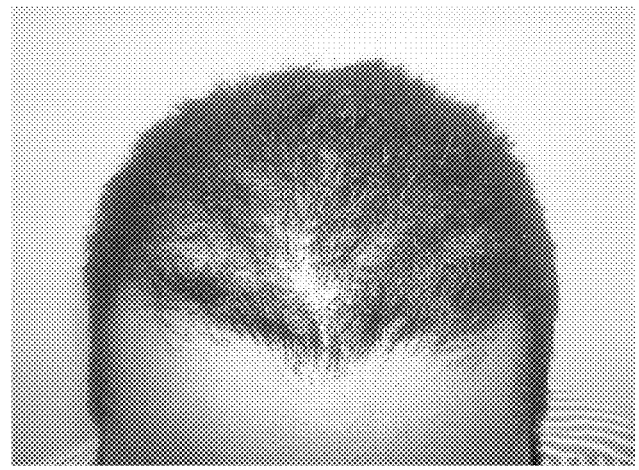
Figure 1E:
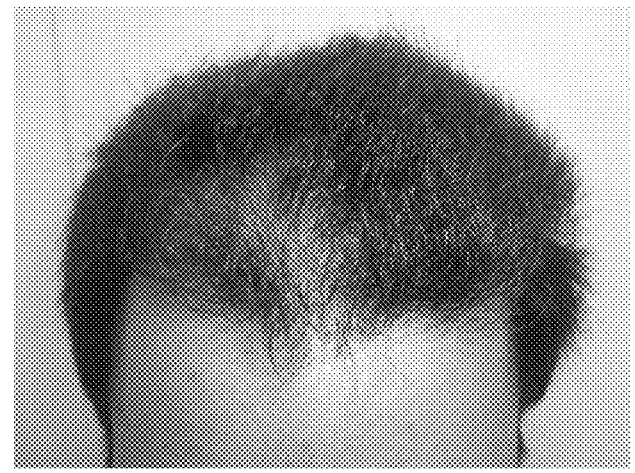
Figure 1F:
Figure 1G:
Figure 1H:
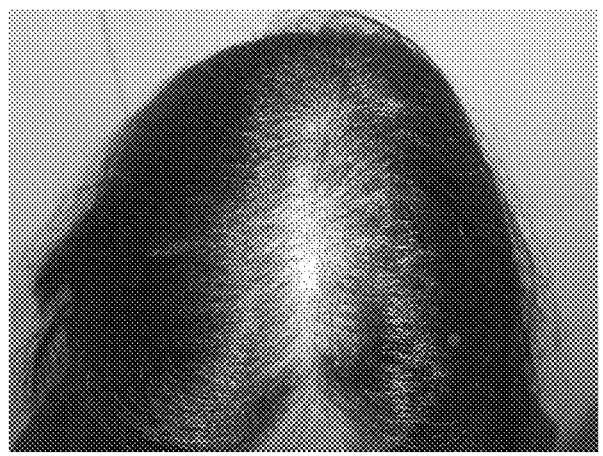
Figure 1I:
Figure 1J:
Figure 1K:
Figure 1L:
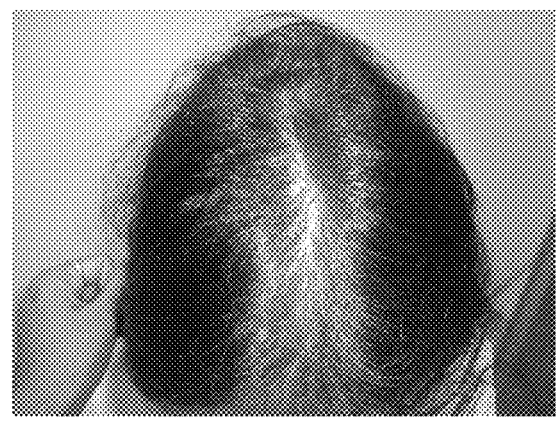

On the contrary, treatment groups receiving the nutrient regimen described above noted early improvement in global photography evaluation within 2 months and reached higher grades of improvement over four months (FIGS. 1(e) and (k) after four months as compared to FIGS. 1(d) and (g) respectively before treatment). There was significant hair growth after completing the study for the period of twelve months (FIGS. 1(f) and (l)).

Patients appreciated the self-assessment scores, as evidenced by the fact that they were allowed to express their concern and rate their results in the form of a score. This scoring system also encouraged interaction of the patients with their friend, family and hair stylist who approved and agreed of noticeable changes in the hair. Thus, the improvement was not only subjective.

The above results prove that without relying on antiandrogens to fight hair loss, the nutrient regimens described herein provided effective treatment that can be followed long term, without fear of side effects. This can instill confidence in patients to continue with the treatment and gain much better outcomes in terms of significant hair growth.

The methods described herein address existing unmet needs for treating hair loss by providing a nutrient treatment regimen that is a better alternate to treatment with Minoxidil, Finasteride, or combinations thereof, which are known to suffer from side effects.

Example 2

Controlled Clinical Trial Comparing Minoxidil with Iron Supplements, and Low Dose Twice a Week Iron, Along with a Nutrient Therapy Regimen in Accordance with One Embodiment Described herein Material and Methods:

The trial consisted of treating twenty women having persistent hair loss in each group. This study was carried out for more than twelve months, and observations and data from the study are presented below.

Group I: The iron therapy group, received application of 2% minoxidil lotion 1 mL, 2 times a day, morning after bath and evening before sleep and intermittent ferrous sulfate equivalent of 100 mg elemental iron once in three days.

Group II: The nutrition treatment regimen group, which received intermittent iron (ferrous bisglycinate 83 mg on the $2^{nd}$ day and 83 mg on the $5^{th}$ day), along with combinations of magnesium hydroxide (100 mg), curcumin (250 mg), vitamin A (2000 IU), vitamin D3 (400 IU), ($1^{st}$ and $4^{th}$ day); the combination comprising lactoferrin (110 mg), vitamin C (200 mg), and folic acid (100 mcg); the combination comprising and melatonin (50 mg), gamma linoleic acid (200 mg), L-histidine hydrochloride (14 mg), glycine (10 mg), lysine mono HCl (25 mg), and pyridoxin HCl (1.5 mg), cyanocobalamin (1 mcg), ($3^{rd}$ and $6^{th}$ day). The group was not treated with scalp application of Minoxidil.

The progress of the groups was recorded on day one and thereafter two, four, six and twelve months. The parameters evaluated were global photography, trichoscopy hair density counts per square centimeter, hair caliber in microns, and patient's personal evaluation score. The hemoglobin levels for group I and group II were monitored every two months until the completion of 6 months.

Independent evaluation of the photographs was done by three different persons, who were blinded about the status of the patient and the group. The photographs were graded for hair density, hair quality, visible changes in the size of the area of thinning or hair loss and any appearance of new hair growth. Scores allotted and results recorded at the end of 6 months are described in Table 5.

TABLE 5

Global Photograph Grades in each group

| Score | Criteria | Improvement in 6 months |
|---|---|---|
| 0 | Worse than before | |
| I | No change | — |
| II | Marginal | 90% of Group l |
| III | Noticeable | 10% of Group l |
| IV | Good | 97% of Group ll |
| V | Very good | 3% of Group ll |

Observations:

TABLE 6

Comparison of Result at 2, 4 & 6 months

| Criteria Evaluated | Group l | | Group ll | | |
|---|---|---|---|---|---|
| | 4 mths | 6 mths | 4 mths | 6 mths | 12 mths |
| Control of Hair fall | 6-8 wks | | 3-4 wks | | |

TABLE 6-continued

Comparison of Result at 2, 4 & 6 months

| Criteria | Group I | | Group II | | |
|---|---|---|---|---|---|
| Evaluated | 4 mths | 6 mths | 4 mths | 6 mths | 12 mths |
| Density | 9% | 16% | 38% | 51% | 62% |
| Caliber | 4% | 8% | 32% | 43% | 49% |
| No Benefit | — | — | — | — | — |
| Worsened | — | — | — | — | — |

Figure 2A:
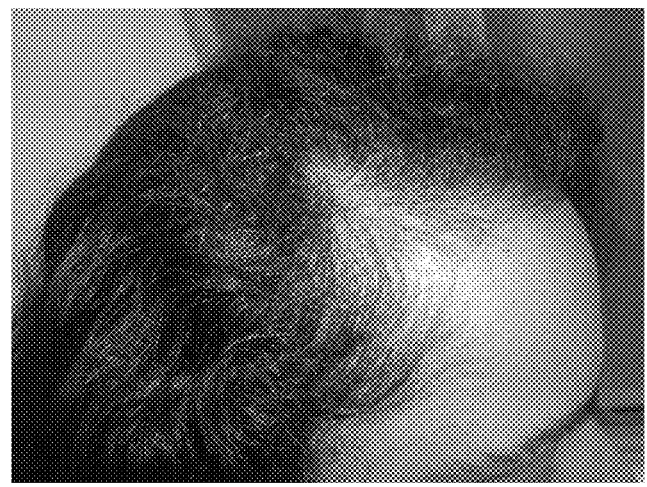
FIG. 2(a) is an image of a female subject with hair loss before treatment.
Figure 2B:
FIG. 2(b) is an image of the same female subject receiving once a day iron treatment throughout the week after two months.
Figure 2C:
FIG. 2(c) is an image of the same female subject receiving once a day iron treatment throughout the week after two months.
Figure 2D:
FIG. 2(d) is an image of the same female subject receiving once a day iron treatment throughout the week after four months.
Figure 2E:
FIG. 2(e) is an image of a female subject with hair loss before treatment according to one embodiment of the methods described herein.
Figure 2F:
FIG. 2(f) is an image of the same female subject receiving nutrient treatment regimen in accordance with one embodiment of the methods described herein after two months.
Figure 2G:
FIG. 2(g) is an image of the same female individual receiving nutrient treatment regimen in accordance with one embodiment of the methods described herein after four months.
Figure 3A:
FIG. 3(a) is an image of a male subject with hair loss before treatment.
Figure 3B:
FIG. 3(b) is an image of the same male subject after four months of treatment with the cyclical therapy.
Figure 3C:
FIG. 3(c) is an image of a female subject with hair loss before treatment.
Figure 3D:
FIG. 3(d) is an image of the same female subject after four months of treatment with cyclical therapy.
Figure 3E:
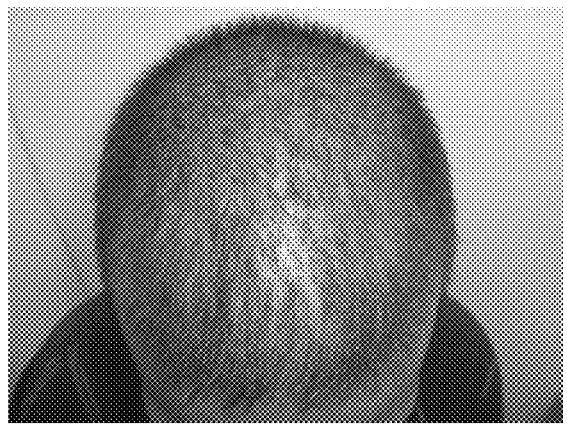
FIG. 3(e) is an image of a male subject with hair loss before treatment.
Figure 3F:
FIG. 3(f) is an image of the same male subject receiving nutrient treatment regimen in accordance with one embodiment of the methods described herein after four months.
Figure 3G:
FIG. 3(g) is an image of a female subject with hair loss before treatment.
Figure 3H:
FIG. 3(h) is an image of the same female subject receiving nutrient treatment regimen in accordance with one embodiment of the methods described herein after four months.

Group I: The standard treatment group following 2% Minoxidil application 1 ml twice a day and intermittent ferrous sulfate (dosed at the equivalent of 100 mg of elemental iron) once in three days, complained of hair loss for 8-10 weeks. The average improvement in density as appreciable to the patients, on measuring closely it was 5% at 4 months (FIG. 2(b) as compared to FIG. 2(a)) and 11% at 6 months (FIG. 2(c)). The average improvement in caliber was none at 2 months, slightly noticeable at 4% only after 4 months, which improved marginally to 8% at the end of 6 months. There were 85% non-responders in the treatment group at 2 months, 66% non-responders at 4 months and 47% non-responders even at the end of 6 months. 3% expressed concern that the hair loss and thinning had worsened than before.

Group II: The intermittent iron plus the nutrient treatment regimen group showed an average improvement in density of 26% at 2 months (not shown in Table 6) and 38% at 4 months, which improved to 46% at 6 months to 52% at 12 months. The average improvement in caliber in the nutrition study group at 2 months was 14% (not shown in Table 6) and at 4 months was 32%, which improved to 39% at the end of 6 months and 43% at the end of 12 months. Hair loss was controlled in all of the patients in group III within 3-4 weeks. All of the twenty women in the study group responded, with varying amounts of improvement, within 2 months of starting the iron plus intermittent nutritional therapy.

Global photography scores in group I varied between grade 0-I in 86% patients and grade II in the remaining 14% patients by the end of 6 months. Photography scores in group II were between I-II in 90% patients and grade III in 10% patients. Group III had 97% patients scoring between grades III and 3% can be rated as grade IV, though none could be rated as grade V.

Group I showed a late response, beginning at 4 months, followed by progress at 6 months. All the twenty women in the study group responded with varying amount of improvement. Scientifically, the data indicates that there are hidden, covert iron deficiencies in patients who are on the lower side of the normal range, which when even minimally supported can lead to clinical changes in hair growth and control of hair fall. However, this group showed the side effect of gastric irritation and constipation. The patients found it difficult to continue the treatment for a longer period, and gave it up after six months.

Group II, using no Minoxidil with intermittent iron once in 3 days plus nutrient combinations, showed 52% improvement in hair density within 6 months which was significantly more enhanced than the results in the Minoxidil plus iron supplement study. The approach provided correction of iron and ensured better utilization of iron along with provision of other hidden nutrient deficiencies in early stages of hair loss. It is also noted that improvement started within 2 months, and there were no non-responders, which suggests efficacy better than 2% Minoxidil which is the presently-approved treatment.

Use of intermittent iron has not been implemented for known clinical nutritional regimens for indication of low iron, anemia or for hair loss management as in the present example.

There is no such regimen for clinical application or for the management of hair loss. This example and clinical evaluation provides proof of benefit from such a well planned regimen with intermittent use of iron supplements twice a week resulting in better biological utilization and preventing any events of adverse effects.

Example 3

Controlled Clinical Trial Comparing Cyclical Nutrient Therapy, and Nutrient Therapy Regimen in Accordance with One Embodiment Described herein Material and Methods:

The trial consisted of treating the 200 men and 200 women having persistent hair loss for more than six months, divided into two groups of 100 each. Presented below are observations and data from this study.

Group I: The group received two supplements per day in 3—day cycles, as per the Cyclical Nutrient Therapy similar to the published studies by the inventor (Rajendrasingh Rajput, "The A Scientific Hypothesis on the Role of Nutritional Supplements for Effective Management of Hair loss and Promoting Hair Regrowth", Journal of Nutritional Health & Food Science May 11, (2018)).

The cyclical nutrition therapy included two supplements per day in 3 day cycles of: antioxidant, calcium carbonate 1000-2000 mg, vitamin D3 1200-1500 IU on Monday and Thursday; iron (ferrous fumarate) 200-300 mg, folic acid 1.8-2 mg, vitamin C 180-150 mg, Omega 3 fatty acid 800-1200 mg on Tuesday and Friday; and essential amino acids (tyrosine 60-80 mg, lysine mono HCl 100-120 mg, glycine 75-100 mg, B-Complex (Vitamin B3 (50-125 mg), Vitamin B12 (15-20 mcg), Vitamin B6 (10-15 mg), biotin (0.5-1 mg)) on Wednesday and Saturday; and medicines or an extra dose of nutrient as per individual status if required on Sunday.

Group II: The group received nutrients as per the treatment regimen and combinations described below without any scalp application of Minoxidil. The nutrient regimen included combinations of curcumin synthetic (250 mg), calcium (500 mg), vitamin A (2000 IU), vitamin D3 (400 IU), and beta-carotene (BASF Australia Ltd., Australia) (30 mg) ($1^{st}$ and $4^{th}$ day); the combination comprising vitamin C (400 mg), Co enzyme Q10 (30 mg), omega 3 fatty acid (VivoMega™, GC Rieber Oils AS, Norway) (300 mg), folic acid (100 mcg) and ferrous bisglycinate (83 mg) ($2^{nd}$ and $5^{th}$ day); the combination comprising and inositol (50 mg), biotin (50 mg), lysine mono HCl (25 mg), L-arginine (125 mg), L-ornithine (75 mg), tyrosine (11.9 mg) and pyridoxin HCl (1.5 mg), cyanocobalamin (1 mcg), nicotinamide (14 mg), para amino benzoic acid (280 mg) on $3^{rd}$ and $6^{th}$ day of week and zinc gluconate 20-40 mg on $1^{st}$ to $6^{th}$ day of week in accordance with the present invention.

The progress of the groups was recorded on day one and thereafter every two months for a period of six months. The parameters evaluated were global photography, trichoscopy hair density counts per centimeter square, hair caliber in microns and patient's personal evaluation score. The hemoglobin levels for group I and group II were monitored every two months until the completion of 6 months.

TABLE 7

Global Photograph Grades in each group

| Score | Criteria | Improvement in 6 months |
|---|---|---|
| 0 | Worse than before | — |
| I | No change | — Group I |
| | | — Group II |
| II | Marginal | 82% of Group I |
| | | — Group II |
| III | Noticeable | 14% of Group I |
| | | 12% of Group II |
| IV | Good | 4% of Group I |
| | | 88% of Group II |
| V | Very good | — Group I |
| | | — Group II |

Observations:

TABLE 8

Comparison of Result at 2, 4 & 6 months

| Criteria | Group I | | | Group II | | |
|---|---|---|---|---|---|---|
| Evaluated | 2 mths | 4 mths | 6 mths | 2 mths | 4 mths | 6 mths |
| Control of Hair fall | | 6-8 wks | | | 3-4 wks | |
| Density | 18% | 30% | 34% | 22% | 38% | 52% |
| Caliber | 9% | 21% | 25% | 12% | 32% | 43% |
| No Benefit | — | — | — | — | — | — |
| Worsened | — | — | — | — | — | — |

Group I: The cyclical therapy group reported reduced hair loss within 6-8 weeks. The average improvement in density was 18% at 2 months and 30% at 4 months. The average improvement in caliber was 9% in 2 months, 21% at 4 months. All patients responded with some improvement within the first 2 months. However, some patients showed the side effect of constipation, requiring perseverance by patients to continue with the treatment. There were no non-responders.

Group II: The nutrient treatment regimen group showed an average improvement in density of 22% at 2 months and 36% and at 4 months which improved to 45% at 6 months. While the average improvement in caliber in the nutrition study group at 2 months was 12% and at 4 months was 29%, which improved to 37% at the end of 6 months. Hair loss was controlled in all the patients in group II, within 3-4 weeks. The nutrient regimen of the present invention also avoids overdose or excess use of nutrients, which could be seen case of some of the ingredients in case of already known cyclical therapy.

The above results prove that the nutrient regimens described herein provided effective treatment that can be followed long term, without fear of side effects. This instilled confidence in patients to continue with the treatment and gain much better outcome in terms of better hair caliber, improvement of hair density and significant hair growth, with much reduced dose of ingredients as compared to cyclical therapy.

Example 4

Controlled Clinical Trial on Female Subjects Suffering from Poly Cystic Ovarian Disease (PCOD) by Treating Hair Loss in Accordance with the Present Disclosure It is observed that female subjects suffering from PCOs also suffer from significant hair loss. However, there is no specific treatment for hair loss due to PCOs.

In the present clinical trial number of cases studied: 18 females

Subjects received combinations of colostrum (Natural Health Organics, Australia) (200 mg), curcumin synthetic (250 mg), calcium (500 mg), vitamin A (2000 IU), vitamin D3 (400 IU), and ($1^{st}$ and $4^{th}$ day); the combination comprising lactoferrin (110 mg), vitamin C (400 mg), Co enzyme Q10 (30 mg), omega 3 fatty acid (VivoMega™, GC Rieber Oils AS, Norway) (300 mg), folic acid (100 mcg) and ($2^{nd}$ and $5^{th}$ day); the combination comprising and melatonin (50 mg), inositol (50 mg), biotin (50 mg), gamma linoleic acid (200 mg), L-histidine hydrochloride (14 mg), L-arginine (125 mg), L-ornithine(75 mg), tyrosine (11.9 mg) and pyridoxin HCl (1.5 mg), cyanocobalamin (1 mcg), nicotinamide (14 mg) and alpha tocopherol (60 mg) ($3^{rd}$ and $6^{th}$ day) in accordance with the present invention. Additionally, subjects also received once a week dose of Vitamin D3 50,000 IU. The group was not treated with scalp application of Minoxidil.

Figure 4A:
FIG. 4(a) is an image depicting hair loss in a female due to PCOD prior to treatment.
Figure 4B:
FIG. 4(b) is an image of the same female depicting PCOD hair loss response and improvement within two months of treatment of hair loss in accordance with one embodiment of the methods described herein.

It was observed that, as compared to the hair loss experienced prior to the treatment (FIG. 4(a)), the response to treatment in terms of curbing hair loss and improving hair growth was noticeable within two months (FIG. 4(b)).

Example 5

Controlled Clinical Trial on Female Subjects Suffering from Hair Loss Due to Thyroid with Treatment of Hair Loss Hyperthyroid state causes hair loss from high metabolic rate, while hypothyroid state has sluggish metabolism. However, currently there is no treatment for hair loss resulting from these conditions.

Number of cases studied: 11 females and 4 males, total 15 cases.

Subjects received combinations of magnesium sulfate (200 mg), colostrum Natural Health Organics, Australia) (200 mg), curcumin synthetic (250 mg), vitamin A (2000 IU), vitamin D3 (400 IU), and beta-carotene (BASF Australia Ltd., Australia) (30 mg) ($1^{st}$ and $4^{th}$ day); the combination comprising vitamin C (400 mg), folic acid (100 mcg) and ferrous bisglycinate (83 mg) ($2^{nd}$ and $5^{th}$ day); the combination comprising biotin (50 mg), gamma linoleic acid (200 mg), L-histidine hydrochloride (7.7 mg), glycine (10 mg), L-arginine (125 mg), L-ornithine(75 mg), tyrosine (11.9 mg) and pyridoxin HCl (1.5 mg), cyanocobalamin (1 mcg), N acetyl cysteine 200 mg ($3^{rd}$ and $6^{th}$ day) in accordance with the present invention. The group was not treated with scalp application of Minoxidil.

Figure 5A:
FIG. 5(a) is an image depicting hair loss in a female due to thyroid dysfunction prior to treatment.
Figure 5B:
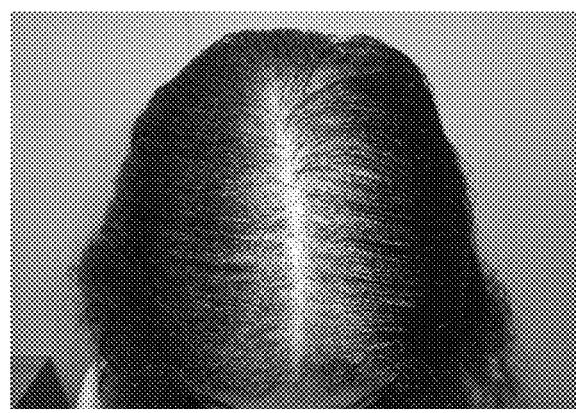
FIG. 5(b) is an image of the same female depicting response and improvement of thyroid-related hair loss within two months following treatment in accordance with one embodiment of the methods described herein.
Figure 5C:
FIG. 5(c) is an image depicting hair loss in another female due to thyroid prior to treatment.
Figure 5D:
FIG. 5(d) is an image of the same female depicting response and improvement to thyroid-related hair loss within two months with treatment in accordance with one embodiment of the methods described herein.

FIG. 5(a) is an image depicting hair loss in a female due to thyroid prior to the treatment and FIG. 5(b): an image of the same female depicting thyroid related hair loss response and improvement within two months with treatment of hair loss in accordance with the present disclosure; FIG. 5(c) is an image depicting hair loss in another female due to thyroid prior to the treatment and FIG. 5(d): an image of the same female depicting thyroid related hair loss response and improvement within two months with treatment of hair loss in accordance with the present disclosure. From these figures, it is apparent that, as compared to the hair loss experienced prior to the treatment, reduction in hair loss and improvement in hair growth was noticeable within two months.

This study demonstrates that providing essential nutrients, amino acids, regulating iron supplement helps restoring hair growth in thyroid induced hair loss.

Example 6

A Controlled Clinical Trial for Treating Hair Loss in Accordance with the Methods Disclosed Herein, where the Hair Loss is Due to Diffuse Alopecia Areata Diffuse hair loss does not follow the pattern distribution of androgen induced, genetic or hereditary hair loss. Hence, this poses challenge in deciding the line of treatment and conventional treatment may not help treat such hair loss.

In this study, the subjects received combinations of magnesium hydroxide (100 mg), colostrum (Natural Health Organics, Australia) (200 mg), vitamin A (2000 IU), and beta-carotene (BASF Australia Ltd., Australia) (30 mg) ($1^{st}$ and $4^{th}$ day); the combination comprising lactoferrin (110 mg), vitamin C (400 mg), Co enzyme Q10 (30 mg), folic acid (100 mcg) and ferrous bisglycinate (83 mg) ($2^{nd}$ and $5^{th}$ day); the combination comprising and biotin (50 mg), gamma linoleic acid (200 mg), L-histidine hydrochloride (7.7 mg), glycine (10 mg), lysine mono HCl (25 mg), L-arginine (125 mg), L-ornithine(75 mg), tyrosine (11.9 mg) and pyridoxin HCl (1.5 mg), cyanocobalamin (1 mcg), nicotinamide (14 mg), para amino benzoic acid (280 mg) ($3^{rd}$ and $6^{th}$ day of the week). Subjects also received once a week dose of Vitamin D3 (50,000 IU) with N acetyl cysteine (200 mg). The treatment was without any scalp application of Minoxidil. Minoxidil is considered the standard treatment for hair loss, but is not successful for treating this type of hair loss.

Figure 6A:
FIG. 6(a) is an image depicting hair loss in a female due to diffuse alopecia areata prior to treatment.
Figure 6B:
FIG. 6(b) is an image of the same female depicting improvement within two months with treatment of hair loss in accordance with one embodiment of the methods described herein.

FIG. 6(a) is an image depicting hair loss in a female due to diffuse alopecia areata prior to the treatment and FIG. 6(b): an image of the same female depicting improvement within two months with treatment of hair loss in accordance with the present disclosure. These figures confirm that the treatment in accordance with the present invention can successfully treat hair loss due to diffuse alopecia areata.

The comprehensive approach of including micronutrients, Vitamin D, thus helps in achieving hair regrowth under conditions of Diffuse Alopecia Areata.

Example 7

Controlled Clinical Trial for Treating Hair Loss in Accordance with the Methods Described herein, for Hair Loss Due to Alopecia Areata Alopecia areata presents with well-defined circumscribed areas of hair loss spots on the scalp, beard or body, resulting from altered immunity and autoimmune response. Mostly, it is treated with local application of drugs like minoxidil in female subjects, or finasteride orally in combination with minoxidil local application in male subjects. However, in view of side effects of these drugs, treatment with alternate regimens is desirable.

The subject received combinations of magnesium hydroxide (100 mg), colostrum Natural Health Organics, Australia) (200 mg), curcumin synthetic (250 mg), calcium (500 mg), vitamin A (2000 IU), vitamin D3 (400 IU), and beta-carotene (BASF Australia Ltd., Australia) (30 mg) Vitamin B55 mg and L-Tryptophan 60 mg ($1^{st}$ and $4^{th}$ day combination comprising lactoferrin (110 mg), vitamin C (400 mg), Co enzyme Q10 (30 mg), omega 3 fatty acid (VivoMega™, GC Rieber Oils AS, Norway) (300 mg), folic acid (100 mcg) and ferrous bisglycinate (83 mg) ($2^{nd}$ and $5^{th}$ day); the combination comprising and melatonin (50 mg), inositol (50 mg), biotin (50 mg), gamma linoleic acid (200 mg), L-histidine hydrochloride (7.7 mg), glycine (10 mg), lysine mono HCl (25 mg), L-arginine (125 mg), L-ornithine(75 mg), tyrosine (11.9 mg) and pyridoxin HCl (1.5 mg), cyanocobalamin (1 mcg), nicotinamide (14 mg), para amino benzoic acid (280 mg) ($3^{rd}$ and $6^{th}$ day of the week). Additionally, subjects also received once a week dose of Vitamin D3 (50,000 IU) with N acetyl cysteine (200 mg) was added in accordance with the present invention. The group was not treated with scalp application of Minoxidil.

Figure 7A:
FIG. 7(a) is an image depicting hair loss in a female due to alopecia areata prior to treatment.
Figure 7B:
FIG. 7(b) is an image of the same female depicting improvement within two months with treatment of hair loss in accordance with one embodiment of the methods described herein.

FIG. 7(a) is an image depicting hair loss in a female due to alopecia areata prior to the treatment and FIG. 7(b): an image of the same female depicting improvement within two months with treatment of hair loss in accordance with the present disclosure. These figures show success of treatment in accordance with the present invention.

The comprehensive regimen approach of including nutrients and Vitamin D, manages to address multiple aspects contributing to the disorder as a whole instead of individually trying to correct or support only one of the many causative factors.

Example 8

Controlled Clinical Trial for Treating Hair Loss in Accordance with the Methods Described herein, where the Hair Loss is Due to Pollution There is no specific treatment for hair loss due to pollution, and inflammation is observed in patients suffering from hair loss due to pollution.

Number of cases studied: 8 males and 4 females, total 12 cases

Subjects received combinations of curcumin synthetic (250 mg), calcium (500 mg), vitamin A (2000 IU .mg), vitamin D3 (400 mg), and beta-carotene (BASF Australia Ltd., Australia) (30 mg) ($1^{st}$ and $4^{th}$ day); the combination comprising lactoferrin (110 mg), vitamin C (400 mg), Co enzyme Q10 (30 mg), omega 3 fatty acid (VivoMega™, GC Rieber Oils AS, Norway) (300 mg) ($2^{nd}$ and $5^{th}$ day); the combination comprising and melatonin (50 mg), gamma linoleic acid (200 mg), glycine (10 mg), lysine mono HCl (25 mg), L-arginine (125 mg), tyrosine (11.9 mg) and pyridoxine HCl (1.5 mg), cyanocobalamin (1 mcg mg), ($3^{rd}$ and $6^{th}$ day of the week). Additionally, subjects also received once a week dose of zinc gluconate (20-40 mg) on $1^{st}$ to $6^{th}$ day of week. The doses of these ingredients were as per Table 1. The group was not treated with scalp application of Minoxidil.

Figure 8A:
FIG. 8(a) is an image depicting hair loss in a female due to pollution prior to treatment.
Figure 8B:
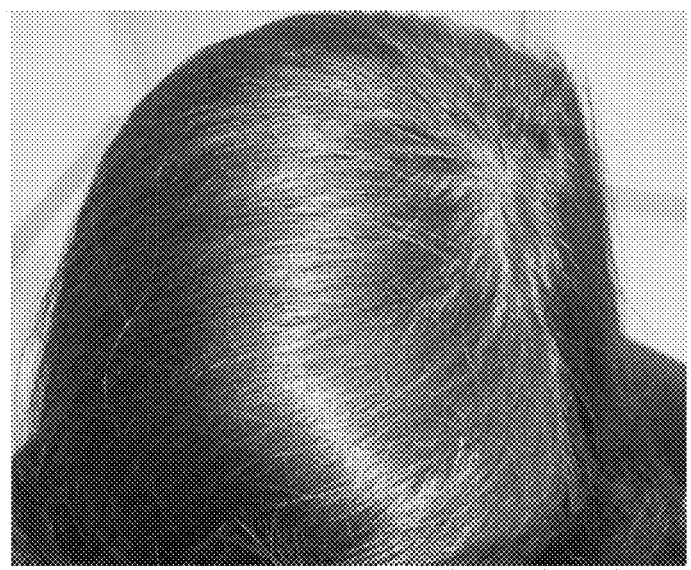
FIG. 8(b) is an image of the same female depicting improvement within two months with treatment of hair loss in accordance with one embodiment of the methods described herein.

FIG. 8(a) is an image depicting hair loss in a female due to pollution prior to treatment and FIG. 8(b): an image of the same female depicting improvement within two months with treatment of hair loss as described above. These results corroborate that the treatment effectively treated hair loss due to pollution.

Though pollution is recognized as a leading cause for hair loss, there is no specific treatment for hair loss due to pollution. This study has demonstrated improvement in scalp status and hair growth with use of nutrients, antioxidants, vitamins, amino acids and immune support, in a safe regimen, without resorting to any medicines and without any overdose or side effects.

Example 9

Controlled Clinical Trial for Treating Hair Loss Due to Miniaturization, Before and After Treatment of Hair Loss in Accordance with the Methods Described Herein Miniaturization of hair refers to the progression of thinning hair. During miniaturization, hair follicles start generating thinner hairs with fragile shafts due to constriction of hair follicles making it harder for the hairs to grow. The less-dense hairs can lead to thinning of hair and consequently balding. There is no satisfactory treatment for such miniaturization currently.

Number of cases studied: 8 males and 4 females, total 12 cases.

The subjects received combinations of magnesium hydroxide (100 mg), colostrum (Natural Health Organics, Australia) (200 mg), curcumin synthetic (250 mg), calcium (500 mg), vitamin A (2000 IU), vitamin D3 (400 IU), and beta-carotene (BASF Australia Ltd., Australia) (30 mg) ($1^{st}$ and $4^{th}$ day); the combination comprising lactoferrin (110 mg), vitamin C (400 mg), Co enzyme Q10 (30 mg), omega 3 fatty acid (VivoMega™, GC Rieber Oils AS, Norway) (300 mg), folic acid (100 mcg) and ferrous bisglycinate (83 mg) ($2^{nd}$ and $5^{th}$ day); the combination comprising and melatonin (50 mg), inositol (50 mg), biotin (50 mg), gamma linoleic acid (200 mg), L-histidine hydrochloride (7.7 mg), glycine (10 mg), lysine mono HCl (25 mg), L-arginine (125 mg), L-ornithine(75 mg), tyrosine (11.9.mg) and pyridoxin HCl (1.5 mg), cyanocobalamin (1 mcg), Nicotinamide (14 mg), para amino benzoic acid (280 mg) ($3^{rd}$ and $6^{th}$ day). Additionally, the subject also received once a week dose of zinc gluconate (20-40 mg) vitamin D3(50,000 IU) and N acetyl cysteine (200 mg) on $1^{st}$ to $6^{th}$ day of week. The subject was not treated with scalp application of Minoxidil.

Figure 9A:
FIG. 9(a) is an image depicting miniaturization of hair of a male individual prior to treatment.
Figure 9B:
FIG. 9(b) is an image of the same male individual depicting miniaturization reversed within two months with treatment of hair loss in accordance with one embodiment of the methods described herein.

The effect of the treatment is shown in FIGS. 9(a) and (b). FIG. 9(a) is an image depicting miniaturization of hair of a male individual prior to the treatment and FIG. 9(b): an image of the same male individual depicting miniaturization reversed within two months with treatment of hair loss in accordance with the present disclosure.

Example 10

Controlled Clinical Trial for Treating Hair Loss in Accordance with the Methods Described herein, wherein the Hair Loss is Due to Smoking Arrest of hair growth is observed in case of smokers leading to hair loss. There is no specific line of treatment available for smokers as such. The current line of treatments relies on minoxidil, which is not found to be very satisfactory.

Number of cases studied: 7 males and 2 females, total 9 cases.

Subjects received combinations of magnesium hydroxide (100 mg), colostrum (Natural Health Organics, Australia) (200 mg), curcumin synthetic (250 mg), vitamin A (2000 IU mg), and beta-carotene (BASF Australia Ltd., Australia) (30 mg) ($1^{st}$ and $4^{th}$ day); the combination comprising lactoferrin (110 mg), vitamin C (400 mg), omega 3 fatty acid (VivoMega™, GC Rieber Oils AS, Norway) (300 mg), folic acid (100 mcg) and ferrous bisglycinate (83 mg) ($2^{nd}$ and $5^{th}$ day); the combination comprising and melatonin (50 mg), biotin (50 mg), gamma linoleic acid (200 mg), L-histidine hydrochloride (7.7 mg), glycine (10 mg), lysine mono HCl (25 mg), L-arginine (125 mg), L-ornithine(75 mg), tyrosine (11.9 mg) and pyridoxine HCl (1.5 mg), cyanocobalamin (1 mcg mg), Nicotinamide (14 mg), ($3^{rd}$ and $6^{th}$ day of the week). Additionally, the subject also received a once a week dose of vitamin D3 (50,000 IU) with N acetyl cysteine (200 mg). The group was not treated with scalp application of Minoxidil.

Figure 10A:
FIG. 10(a) is an image depicting hair loss due to smoking in a male individual prior to treatment.
Figure 10B:
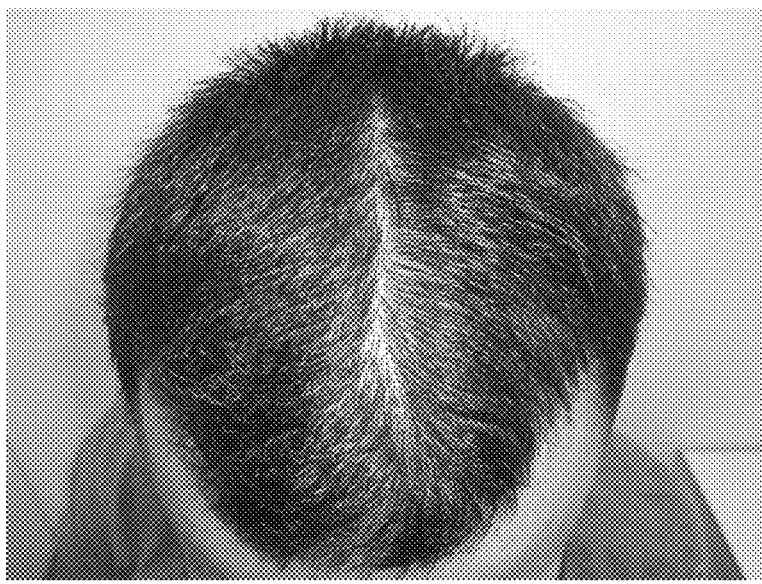
FIG. 10(b) is an image of the same male individual depicting improvement within two months with treatment of hair loss in accordance with one embodiment of the methods described herein.

Successful treatment of hair loss and positive growth was observed after the treatment, as shown in FIGS. 10(a)-(b). FIG. 10(a) is an image depicting hair loss due to smoking in a male individual prior to treatment and FIG. 10(b) is an image of the same male individual depicting improvement within two months of treating hair loss.

Example 11

Controlled Clinical Trial of Treating Hair Loss Due to Male Pattern Hair Loss in the Vertex Area, Before and After Treating Hair Loss in Accordance with the Methods Described Herein Male pattern hair loss is brought on by the presence of hormone receptors in the hair roots of the non-permanent areas. The receptors are stimulated by the male hormone dihydrotestosterone (DHT), and when this happens, the hair loss process begins. Though considered to be treatable, there has not been much success in treating such male pattern baldness.

Number of cases studied: 1 male.

The subject received combinations of magnesium hydroxide (100 mg), colostrum (Natural Health Organics, Australia) (200 mg), curcumin synthetic (250 mg), calcium (500 mg), vitamin A (2000 IU), vitamin D3 (400 IU), and beta-carotene (BASF Australia Ltd., Australia) (30 mg) ($1^{st}$ and $4^{th}$ day); the combination comprising lactoferrin (110 mg), vitamin C (400 mg), Co enzyme Q10 (30 mg), omega 3 fatty acid (VivoMega™, GC Rieber Oils AS, Norway) (300 mg), folic acid (100 mcg) and ferrous bisglycinate (83 mg) ($2^{nd}$ and $5^{th}$ day); the combination comprising and melatonin (50 mg), inositol (50 mg), biotin (50 mg), gamma linoleic acid (200 mg), L-histidine hydrochloride (7.7 mg), glycine (10 mg), lysine mono HCl (25 mg), L-arginine (125 mg), L-ornithine(75 mg), tyrosine (11.9.mg) and pyridoxin HCl (1.5.mg), cyanocobalamin (1 mcg), nicotinamide (14 mg), para amino benzoic acid (280 mg) ($3^{rd}$ and $6^{th}$ day). The subject also received once a week dose of zinc gluconate (20-40 mg) on $1^{st}$ to $6^{th}$ day of week. The individual was not treated with scalp application of Minoxidil.

Figure 11A:
FIG. 11(a) is an image depicting hair loss due to trichotillomania in a male individual prior to treatment.
Figure 11B:
FIG. 11(b) is an image of the same male individual depicting improvement within two months with treatment of hair loss in accordance with one embodiment of the methods described herein.
Figure 11C:
FIGS. 11(c)-(d) are images of the same male individual shown in FIG. 11(b), depicting significant improvement in hair growth around four and six months following treatment of hair loss.
Figure 11D:

FIG. 11(a) is an image depicting male pattern hair loss in vertex area in a male individual prior to the treatment. FIGS. 11(b)-(d) are an image of the same male individual depicting significant improvement in hair growth around two, four and six months following treatment of hair loss.

The treatment regimens methods described herein have been found to be equally effective in males and females. Benefit has been established in several types of hair loss, without using minoxidil or finasteride. In addition, the methods reduce the overdose or excess use of nutrients, regardless of the type of hair loss, including male pattern hair loss, female pattern hair loss, hair loss due to pollution, hair loss due to smoking, hair shaft disorders, adjuvant therapy and improving results after hair transplant. An average improvement of 51% within six months was observed across all studies, irrespective of gender, age, cause and grade of hair loss. There were no side effects from low dose nutritional supplements, and there was no deterioration or any non-responders. Benefits were experienced in around two weeks, and became very visible around 1-2 months. The benefits continued as the program was continued beyond 4-6 months.

It was surprisingly observed that including curcumin, colostrum, lactoferrin, and beta carotene, one by one in rotation every successive day or in successive treatment regimens every month, or changing the iron salt to ferrous bisglycinate, the calcium salt to calcium aspartate and calcium orate, and the zinc salt to zinc gluconate, and including magnesium and selenium salts, delivered unexpected benefits.

The treatment regimens described herein not only curbed hair loss, which can be experienced within two weeks of starting the treatment, but also improved the quality and growth of existing hair and prevented further progress of hair loss, irrespective of the cause and type of hair loss.

Patients reported other health benefits like better skin quality, better nail quality, better sleep, waking up fresh in the morning, relief from minor aches and pains, improvement in thyroid status, improvement in PCOS condition, better energy levels and relief from fatigue. Further, some teenagers observed a growth spurt, and some athletes noticed better stamina.

In various embodiments, methods of providing these health benefits are also disclosed. That is, the compositions and treatment regimens described herein can be used to improve skin quality, improve nail quality, improve sleep, relieve minor aches and pains, improve thyroid function, improve PCOS condition, increase energy levels, or relieve fatigue.

REFERENCES

Beard J L. Effectiveness and strategies of iron supplementation during pregnancy. Am J Clin Nutr., May; 71(5 Suppl) (2000).

Blume-Peytavi U, Blumeyer A, Tosti A, Finner A, Marmol V, Trakatelli M, Reygagne P, Messenger A; European Consensus Group. S1 guideline for diagnostic evaluation in androgenetic alopecia in men, women and adolescents. Br J Dermatol. Jan; 164(1):5-15 (2011).

Davis D R, Epp M D, Riordan H D. Changes in USDA food composition data for 43 garden crops, 1950 to 1999. Journal of the American College of Nutrition., 23:669-682, (2004).

Eisenberg M D, Avery R J, Cantor J H. Vitamin panacea: Is advertising fueling demand for products with uncertain scientific benefit?. *J Health Econ.*, 55:30-44 (2017).

Elena Gammella, Stefania Recalcati, Gaetano Cairo, "Dual Role of ROS as Signal and Stress Agents: Iron Tips the Balance in favor of Toxic Effects", Oxidative Medicine and Cellular Longevity, vol. 2016, Article ID 8629024, 9 pages, (2016).

Guarrera M, Rebora A. The Higher Number and Longer Duration of Kenogen Hairs Are the Main Cause of the Hair Rarefaction in Androgenetic Alopecia. Skin Appendage Disord., 5(3):152-154, (2019)).

Ioannis Delimaris, "Adverse Effects Associated with Protein Intake above the Recommended Dietary Allowance for Adults", International Scholarly Research Notices, vol. 2013, Article ID 126929, 6 pages, (2013).

Kiguradze et al., Persistent erectile dysfunction in men exposed to the 5a-reductase inhibitors, finasteride, or dutasteride, (2017).

Koyama T, Kobayashi K, Wakisaka N, Hirayama N, Konishi S, Hama T, Takeda K, Nakamizo Y, Kawakami M. Eleven pairs of Japanese male twins suggest the role of epigenetic differences in androgenetic alopecia. Eur J Dermatol. January-February; 23(1):113-5, (2013).

Lee, Kee Hyuck et al. "Relationships between Dietary Habits and Allostatic Load Index in Metabolic Syndrome Patients." Korean journal of family medicine vol. 34, 5: 334-46, (2013).

Sadick N S, Callender V D, Kircik L H, Kogan S. New Insight Into the Pathophysiology of Hair Loss Trigger a Paradigm Shift in the Treatment Approach. J Drugs Dermatol. Nov. 1; 16(11) (2017).

Rogovik A L, Vohra S, Goldman R D. Safety considerations and potential interactions of vitamins: should vitamins be considered drugs? Ann Pharmacother; 44:311-24, (2010).

From the foregoing, it will be appreciated that, although specific embodiments of the invention have been described herein merely for purposes of illustration, various modifications may be made without deviating from the spirit and scope of the invention and should not be construed so as to limit the scope of the invention or the appended claims in any way.

What is claimed is:

1. A method of treatment of hair loss, the method comprising periodically administering to a person in need thereof a composition comprising therapeutically effective amounts of three combinations, each combination comprising therapeutically effective amounts of components, wherein the combinations and their components are:
   a) a combination comprising a magnesium salt, colostrum, curcumin, a calcium salt, vitamin A, vitamin D3, and beta-carotene;
   b) a combination comprising lactoferrin, vitamin C, Co enzyme Q10, an omega 3 fatty acid, folic acid and one or more ferrous salts; and
   c) a combination comprising melatonin, inositol, biotin, gamma linoleic acid, one or more amino acids, and one or more B vitamins, wherein combinations a, b, and c are separately administered on one or more pre-determined treatment days of a week, with one or more intermittent non-treatment days in the week for the same ingredient or combination.

2. The method of claim 1, wherein the number of non-treatment days in a week is greater than the number of treatment days in week.

3. The method of claim 1, wherein combinations a, b, and c are each administered more than once per week, with the proviso that none of the combinations are administered simultaneously on the same day.

4. The method of claim 1, wherein the treatment regimen comprises administering a zinc salt concomitantly, separately or sequentially with combinations a, b, and c.

5. The method of claim 4, wherein the zinc salt is administered on one or more treatment days.

6. The method of claim 4, wherein the zinc salt is administered on one or more non-treatment days.

7. The method of claim 4, wherein the zinc salt is administered on six days per week.

8. The method of claim 4, wherein the treatment regimen comprises administering a nutrient combination comprising therapeutically effective amounts of colostrum, lactoferrin, vitamin D3, N acetyl cysteine, and vitamin B12 on one of the non-treatment days to an individual in need thereof.

9. The method of claim 1, wherein the administration of combinations a, b, and c are spaced apart by a period of one, two or three days from each other, with the proviso that all three combinations are administered within the same week and each combination is administered one or two times in a week.

10. The method of claim 1, wherein the administrations of combinations of ingredients comprising therapeutically effective amounts of magnesium, colostrum, curcumin, calcium, vitamin A, vitamin D3, and beta-carotene can be administered on the treatment day 1 and subsequently on the third or fourth day of the same week, with a proviso that no other combination of ingredients is administered on the same third or fourth day, the third or fourth day thereby being a treatment day.

11. The method of claim 1, wherein combination b is administered on treatment day 2 and subsequently on treatment day 4 or 5 of the same week, with a proviso that neither of combinations a or c are administered on the same days.

12. The method of claim 1, wherein combination c is administered on treatment day 3, and subsequently on treatment day 5 or 6 of the same week, with the proviso that neither of combinations a and b are administered on the same days.

13. The method of claim 1, wherein the treatment regimen further includes administering on one or more pre-determined treatment days or non-treatment days therapeutically effective amounts of one or more additional nutrient ingredients not present in combinations a, b, or c, wherein the nutrient ingredients are selected from the group consisting of minerals, vitamins, antioxidants, amino acids, fatty acids, adjuvants, and combinations thereof, which are not present in combinations a, b, or c.

14. The method of claim 1, wherein the calcium salt is a combination of two or more calcium salts.

15. The method of claim 14, wherein the combination of calcium salts comprises calcium aspartate and calcium orate.

16. The method of claim 1, wherein the ferrous salt is ferrous bis-gluconate.

17. The method of claim 1, wherein the zinc salt is zinc gluconate.

18. The method according to claim 1, wherein the administration of antioxidants, omega-3 fatty acid, and amino acid does not exceed two or three days in a week.

19. The method of claim 1, wherein the individual nutrient ingredients in combinations a, b and c, and their dosages, are selected from the group consisting of:
between about 180 mg and about 240 mg of colostrum;
between about 40 mg and about 80 mg of magnesium present in the magnesium salt;
between about 40 mg and about 80 mg of calcium present in the calcium salt,
between about 75 mg and about 110 mg of a ferrous salt,
between about 100 mg and about 200 mg of a selenium salt,
between about 180 mg and about 240 mg of cucurmin curcumin,
between about 50 and 250 mg of beta-carotene,
between about 100 and 150 mg of lactoferrin,
between about 2 and about 5 mg melatonin,
between about 25 and about 50 mg Co enzyme Q10,
between about 400 and about 1100 mg of an omega 3 fatty acid,
between about 1 mg and about 2 mg of alpha lipoic acid,
between about 10 and about 25 mg or gamma linoleic acid,
between about 180 and about 400 mg N acetyl cysteine,
between about 20 and about 60 mg tyrosine,
between about 20 and about 55 mg lysine,
between about 10 and about 25 mg L-ornithine,
between about 125 and about 250 mg L-arginine,
between about 2 and about 5 mg L-histidine,
between about 180 and about 350 mg taurine,
between about 40 and about 120 mg glycine,
between about 10 and about 25 mg para amino benzoic acid,
between about 1 and about 1.8 mg folic acid,
between about 4 and about 12 mg inositol,
between about 4 and about 7 mg biotin,
between about 10 and about 24 mg nicotinamide,
between about 2 and about 4 mg pyridoxine HCl,
between about 60 and about 120 mg calcium D-pantothenate,
between about 8 and about 20 mcg vitamin B12,
between about 70 and about 120 mg vitamin C,
between about 350 and 450 IU vitamin D3,
between about 1200 IU and about 2500 IU vitamin A,
between about 60 and about 210 mg vitamin E,
between about 125 mg and about 200 mg of MSM,
between about 0.5 and about 2 mg of a copper salt,
between about 1 and about 2 mg of a manganese salt,
between about 80 and about 160 mg of an iodide salt,
between about 0.5 and about 1.5 mg of a molybdenum salt,
between about 10 and about 25 mg of a vanadium salt,
between about 125 and 250 mg chromium polynicotinate,
between about 80 and about 160 mg catechin, and
between about 50 and about 80 mg of proanthocyanidin.

* * * * *